United States Patent [19]

Vogelstein et al.

[11] Patent Number: 5,401,828
[45] Date of Patent: Mar. 28, 1995

[54] STRUCTURAL ALTERATIONS OF THE EGF RECEPTOR GENE IN HUMAN GLIOMAS

[75] Inventors: Bert Vogelstein, Baltimore, Md.; Darell Bigner, Chapel Hill, N.C.

[73] Assignees: The Johns Hopkins University, Baltimore, Md.; Duke University, Durham, N.C.

[21] Appl. No.: 991,286

[22] Filed: Dec. 15, 1992

Related U.S. Application Data

[60] Division of Ser. No. 627,869, Dec. 17, 1990, Pat. No. 5,212,290, which is a division of Ser. No. 531,410, Jun. 1, 1990, abandoned, which is a continuation-in-part of Ser. No. 404,226, Sep. 8, 1989, abandoned.

[51] Int. Cl.[6] .................... C07K 5/00; C07K 7/00; C07K 15/00; C07K 3/00
[52] U.S. Cl. ................... 530/300; 530/324; 530/330; 530/327; 530/402; 530/810; 530/812; 530/403; 530/350
[58] Field of Search ............... 530/327, 350, 324, 330, 530/402, 403, 810, 812, 300

[56] References Cited

PUBLICATIONS

Kris et al. Cell vol. 40:619 1985.
Bullard et al. J. Neurosurg. 64:257 1986.
Humphrey et al. Cancer Research 48:2231–2238, 1988.
Genes, and Growth Factors Edited by: Guroff, G. 12th Edition. Chapter 2, pp. 40–76, Wiley, New York.
Lax, I., Brugess, W. H., Bellot, F., Ullrich, A., Schlessinger, J., Givol, D. (1988). Localization of a Major Receptor Binding Domain in the Epidermal Growth Factor by Affinity Labelling. Molecular and Cellular Biology 8:1831–1834.
Lee et al. (1988). Therapeutic Efficacy of Antiglioma Mesenchymal Extracellular Matrix [131]I-Radiolabeled Murine Monoclonal Antibody in a Human Glioma Xenograft Model. Cancer Research 48:539–566.
Lehrman, M. A., Schneider, W. J., Sudhof, T. C., Brown, M. S., Goldstein, J. L., Russell, D. W. (1985). Mutation in LDL Receptor: Alu–Alu Recombination Deletes Exons Encoding Transmembrane and Cytoplasmic Domains. Science 227:140–146.
Malden, L. T. Novak, U., Kaye, A. H., Burgess, A. W.

(List continued on next page.)

Primary Examiner—David L. Lacey
Assistant Examiner—Lila Feisee
Attorney, Agent, or Firm—Banner, Birch, McKie & Beckett

[57] ABSTRACT

The epidermal growth factor receptor (EGFR) gene is amplified in 40% of malignant gliomas and the amplified genes are frequently rearranged. The genetic alterations associated with these rearrangements are characterized in five malignant gliomas. In one tumor, the rearrangement resulted in the deletion of most of the extracytoplasmic domain of the receptor, resulting in a hybrid mRNA between new sequences and the truncated EGFR. The predicted amino acid sequence of the protein from this tumor was remarkably similar to that described for several viral erb-B oncogenes. Four other tumors were noted to have internal deletions of the EGF receptor gene. These rearrangements brought about in-frame deletions affecting either of two cysteine-rich domains in the extracytoplasmic portion of the molecule. The clonal nature of these alterations, and the fact that identical alterations were seen in more than one tumor, suggests a role for these mutant receptor proteins in tumorigenesis. Furthermore, these studies document the existence of tumor specific cell molecules resulting from somatic mutation.

12 Claims, 20 Drawing Sheets

PUBLICATIONS (1988). Selective Amplification of the Cytoplasmic Domain of the Epidermal Growth Factor Receptor Gene in Glioblastoma Multiforme. Cancer Research 48:2711–2714.

Merlino, G. T., Ishii, S., Whang, P. J., Knutsen, T., Xu, Y. H., Clark, A. J., Stratton, R. H., Wilson, R. K., Ma, D. P., Roe, B. A. et al. (1985). Structure and Localization of Genes Encoding Aberrant and Normal Epidermal Growth Factor Receptor RNAs from A431 Human Carcinoma Cells. Molecular Cellular Biology 5:1722–1734.

Nilsen, T. W., Maroney, P. A., Goodwin, R., Rottman, R. M., Crittenden, L. B., Raines, M. A. Kung, H. J. (1985). c-erbB Activation in ALV-Induced Erythroblastosis: Novel RNA Processing and Promoter Insertion Results in Expression of an Amino-Truncated EGF Receptor. Cell 41:719–726.

Pelley, R. J., Moscovici, C., Hughes, S., Kung, H. J. (1988). Proviral—Activated c-erbB is Leukemogenic but not Sarcomagenic: Characterization of a Replication-Competent Retrovirus Containing the Activated c-erbB. Journal of Virology 62:1840–1844.

Raines, M. A., Lewis, W. G., Crittenden, L. B., Kung, M. J. (1985). c-erbB Activation in Avian Leukosis Virus-Induced Erythroblastosis: Clustered Integration Sites and the Arrangement of Provirus in the c-erbB Alleles. Proc. Natl. Acad. Sci. USA 82:2287–2291.

Riedel, H., Massoglia, S., Schlessinger, J., Ullrich, A. (1988). Ligand Activation of Overexpressed Epidermal Growth Factor Receptors Transforms NIH 3T3 Mouse Fibroblasts. Proc. Natl. Acad. Sci. USA 85:1477–1481.

Ullrich, A., Coussens, L., Hayflick, J. S., Dull, T. J., Gray, A., Tam, A. W., Lee, J., Yarden, Y., Liebermann, T. A., Schlessinger, J., et al. (1984). Human Epidermal Growth Factor Receptor cDNA Sequence and Aberrant Expression of the Amplified Gene in A431 Epidermoid Carcinoma Cells. Nature 309:418–425.

Vogelstein, B., Fearon, E. R., Hamilton, S. R., Preisiger, A. C., Willard, H. F., Michelson, A. M., Riggs, A. D., Orkin, S. H. (1987). Clonal Analysis Using Recombinant DNA Probes from the X-Chromosome. Cancer Research 47:4806–4813.

Wong, A. J., Bigner, S. H., Bigner, D. D., Kinzler, K. W., Hamilton, S. R., Vogelstein, B. (1987). Increased Expression of the Epidermal Growth Factor Receptor Gene in Malignant Gliomas is Invariably Associated with Gene Amplification. Proc. Natl. Acad. Sci. USA 84:6899–6903.

Xu, Y. H., Ishii, S., Clark, A. J., Sullivan, M., Wilson, R. K., Ma, D. P., Roe, B. A., Merlino, G. T. Pastan, I. (1984). Human Epidermal Growth Factor Receptor cDNA is Homologous to a Variety of RNAs Overproduced in A431 Carcinoma Cells. Nature 309:806–810.

Yamamoto, G., Hihara, H., Nishida, T., Kawai, S., Toyashima, K. (1983). A New Avain Erythroblastosis Virus, AEV-H Carries erbB Gene Responsible for the Induction of Both Erythroblastosis and Sarcoma. Cell 34:225–232.

Yamazaki, H., Fukui, Y., Ueyama, Y., Tamaoki, N., Kawamoto, T., Taniguchi, S., Shibuya, M. (1988). Amplification of the Structurally and Functionally Altered Epidermal Growth Factor Receptor Gene (c-erbB) in Human Brain Tumors. Molecular and Cellular Biology 8:1816–1820.

Zengerling, S., Tsui, L. C., Grzeschik, K. H., Olek, K., Riordan, J. R., Buchwald, M. (1987). Mapping of DNA Markers Linked to the Cystic Fibrosis Locus on the Long Arm of Chromosome 7 [Published Erratum Appears in Am J Hum Genet 1987 Aug.:41(2):330] Am. J. Hum. Genet. 40:228–236.

Haley et al. The Human EGF Receptor Gene: Structure of the 110 kb Locus and Identification of Sequences Regulating its Transcription, *Oncogene Research*, 1:375–396 (1987).

Haley et al., Analysis of Mammalian Fibroblast Transformation by Normal and Mutated Human EGF Receptors, *Oncogene*, 4:273–283 (1989).

Nister et al., Expression of Messenger RNAs for Platelet-derived Growth Factor and Transforming Growth Factor-and Their Receptors in Human Malignant Gliomas Cell Lines, *Cancer Research*, 48:3910–3918 (1988).

Steck et al., Expression of an Altered Epidermal Growth Factor Receptor by Human Glioblastoma Cells, *Cancer Research*, 48:5433–5439 (1988).

(List continued on next page.)

PUBLICATIONS

Velu et al., Epidermal Growth Factor-Dependent Transformation by a Human EGF Receptor Proto-Oncogene, *Science,* 238:1408–1410 (1987).

Wells et al., Genetic determinants of neoplastic transformation by the retroviral oncogene v-erbB, *Proc. Natl. Acad. Sci. USA,* 85:7597–7601 (1988).

Wong et al., "Internal Deletions of the EGF Receptor Gene in Primary Human Gilomas," J. Cell Biochem., Supp. 13B, p. 149, 1989.

Humphrey et al., "Amplification and Expression of Mutant Epidermal Growth Factor Receptor Genes in Human Gliomas." J. Neurooncol., suppl., vol. 7, p. 515 (1989).

Bigner et al., "Characterization of the Epidermal Growth Factor Receptor in Human Glioma Cell Lines and Xenografts," C. Research 50, 8017–8022, 1990.

Humphrey et al., "Anti-synthetic peptide antibody reacting at the fusion junction of deletion-mutant epidermal growth factor receptors in human glioblastoma," Proc. Natl. Acad. Sci. USA, 87, pp. 4207–4211 (1990).

Yamazaki, et al., "Amplification of the Structurally and Functionally Altered Epidermal Growth Factor Receptor Gene (c-erbB) in Human Brain Tumors", *Molecular and Cellular Biology,* 8(4):1816–1820 (Apr. 1988).

Gentry, et al., "Characterization of Site-Specific Antibodies to the erbB Gene Product and EGF Receptor:Inhibition of Tyrosine Kinase Activity", *Virology,* 152:421–421 (1986).

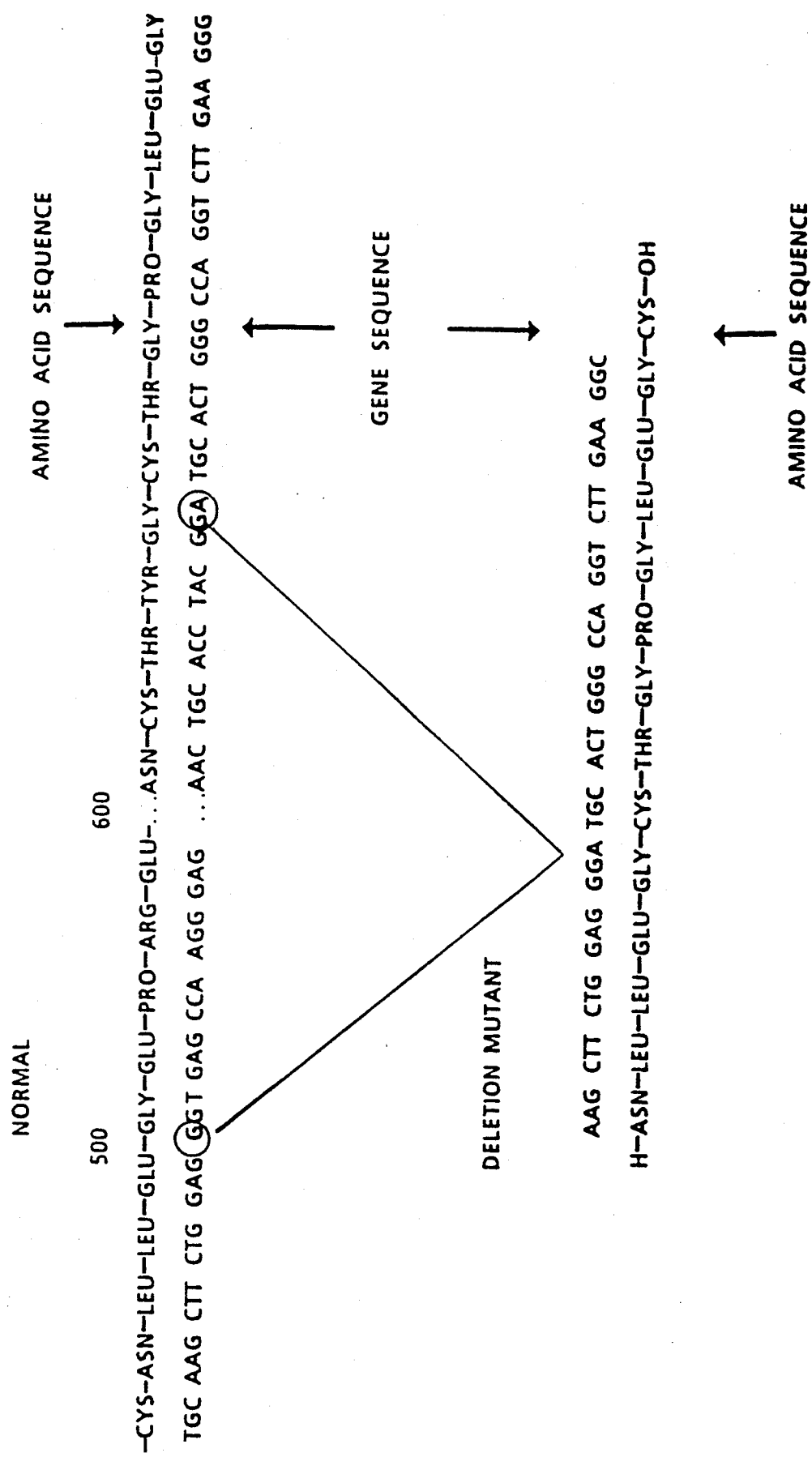
FIG. I

FIG. 2

NORMAL

AMINO ACID SEQUENCE →

-LEU-GLU-GLU-LYS-LYS-VAL-CYS-GLN-GLY-THR ... VAL-LYS-LYS-CYS-PRO-ARG-ASN-TYR-VAL-VAL-THR-ASP-HIS
 1                          5                                   270              275                         280
CTG GAG GAA AAG AAA GTT TGC CAA GGC ACG ... GTG AAG AAG TGT CCC CGT AAT TAT GTG GTG ACA GAT CAC

← GENE SEQUENCE →

DELETION MUTANT

CTG GAG GAA AAG AAA GGT AAT TAT GTG GTG ACA GAT CAC
H-LEU-GLU-GLU-LYS-LYS-GLY-ASN-TYR-VAL-VAL-THR-ASP-HIS-CYS-OH

GLIOMA FUSION PEPTIDE

← AMINO ACID SEQUENCE

FIG. 3

543   DELETION MUTANT

NH$_2$—MET—ASN—ILE—THR—CYS—THR—GLY—ARG—GLY—PRO—ASP—ASN—CYS—OH    AMINO ACID SEQUENCE

AGT AAC ATC ACC TGC ACA GGA CGG GGA CCA GAC AAC TGT    GENE SEQUENCE

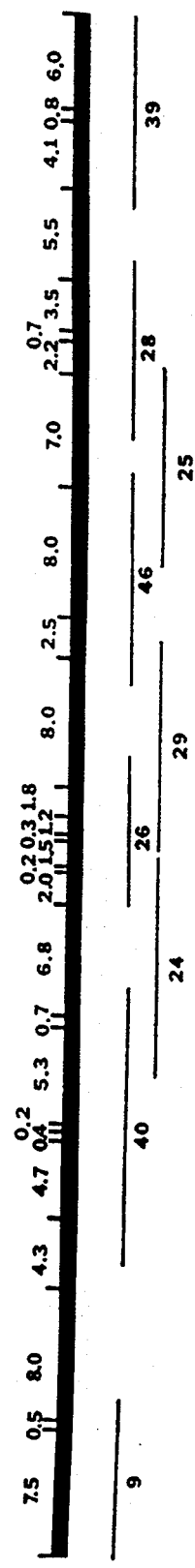
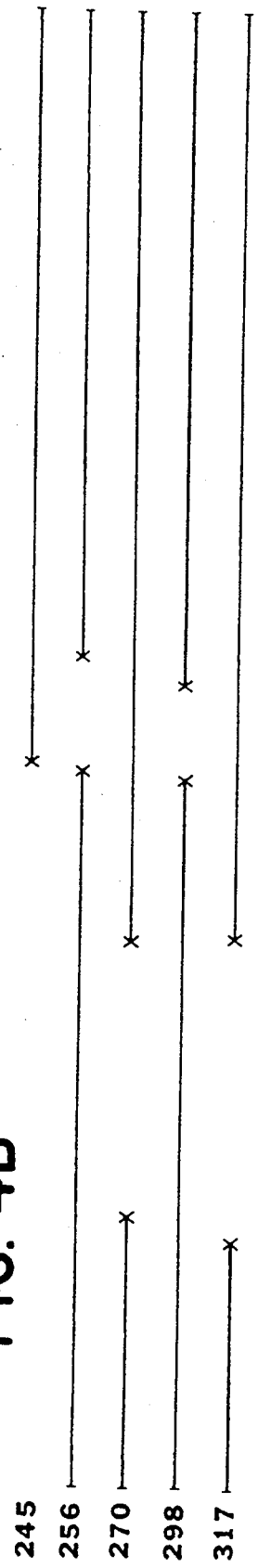
FIG. 4A
FIG. 4B

FIG. 5B(I)

```
EG      AAAAAAACAACAACTATAAGCAAGTAAAAAGACATGTCAAGTTGAAAAAAATATTTGCCACTCGAATTAC
             ::::::::: ::::::::::::::::::::::::::::::::::::::::::::::::::::::::
D245    AAAAAACAACAACTATAAGCAAGTAAAAAGACATGTCAAGTTGAAAAAATATTTGCCACTCGAATTAC     75

EGFR    TTAGTAGAGACGGGGTTTCACCACGTTGGCCAGGCTGGTCTCAAACTCCTGACCTCAAGTGATCTGCCCGCCTCG
                                            ───────────────────────────►
                                                        Alu

TEG     AGTGGTCTCATCTTTCTAATATATAAATACTT
        :::::::::::::::::::::::::::::::
D245    AGTGGTCTCATCTTTCTAATATATAAATACTTCTAATATAAAATACTTCTAATATAAAATACT|CTAATA     150
                └─────rpt1─────┘└─────rpt2─────┘└─────rpt3─────┘

EGFR    GCCTCCCAAGTGTTGGGATTATAGGCATAAGCCACTGCACCCAGCCAAGGCACACACTTTGGAGAATAAACACT
        ◄───────────────────────────
                    Alu
```

FIG. 5B(2)

```
                         Break point                                              Alu
                                                                                  ──→
TEG    CTCTAAATCAGCAAGAGATTAGGAGTCCAACAGAAAAGGTACAAAGACCAGGACAGTGGC        225
       ::::::::::::::::::::::::::::::::::::::::::::::::::::::::::::
D245   TATAAATACTTCTCTAAATCAGCAAGAGATTAGGTGATTTAGCAGAGTCCAGTCTTACTGACAAACAGCCGTAC
            rpt4                                ::::::::::::::::::::::::::::::
EGFR                       CCTGTTCGCTGCTGAGGGTAGAACTGTGCTTGACTACTAGGCAGAGTCCAGTCTTACTGACAAACAGCCGTAC Alu
                                                              ──→
TEG    TCATGCCTGTAATCCCAGCACTTTGGGAGGCTGAGGCAGGCTGATCACTTGAGGTCAGGAGTTTGAGACAAGTGT
       ::::::::::::::::::::::::::::::::::::::::::::::::::::::::::::::::::::::::
D245   ATCTGTTCTGTCTTTTCAATCAAACATCAGTTCTGCTTAACATTGATGTGTACATCTTGAGGATGTCAAAAT   300
       ::::::::::::::::::::::::::::::::::::::::::::::::::::::::::::::::::::::::
EGFR   ATCTGTTCTGTCTTTTCAATCAAACATCAGTTCTTGCTTAACATTGATGTGTACATCTTGAGGGATGTCAAAAT Alu
                                                    ──→
TEG    GACCAACTTGGTGCAACTTCATCTCTACCAAAATACAAAAATTAGCTGGGGAC
       ::::::::::::::::::::::::::::::::::::::::::::::::::::
D245   ATTGTAAGCTAAGTTTTTCATACCTGTGTTCCACACTCACCATTTTAGTAATAA                    355
       ::::::::::::::::::::::::::::::::::::::::::::::::::::
EGFR   ATTGTAAGCTAAGTTTTTCATACCTGTTCCACACTCACCATTTTAGTAATAA
```

FIG. 6

```
D245      GCCAGCGTCTTGCGCCGCCATTGCGGGAGGCTGTCCTCAGAGCAGGTCTGGCGCCCGGTGGCTGGACCGGCCCCA     75

D245      GGAGCCCAGTCACCGGGCGTCATTGGCTCAGGCTGCGGGGCCCTCGGCACCTTCTCCCGCCCCGGGGTTCCCACG    150

D245      CGGCGGGCGGCGGCGGCGGCGGCGGCGTCAGGGGCGGAGCCTGCCGAAGCGCCCTTTGTCTGCGGAGGTCAACAT    225

D245      ACCTGGCCTAAGGAGGCAGATTGAGTGACTCTCACTCACCACTGGTGTTGCTCTTTGAAAGTGGCGCTTGGCACC    300

D245      AGCATGAACTCCCCATCCTCAGCAATCCCATCAGGTGTTTTGGGTCTTCAACCTAAAATTCTATCTTACAAGATC    375

D245      CTTGCCAGGATGCAGATTTGAATACTATAGTGAAGTCTGTACATGAAGAAATGATGCTTTTAGGGAGGAAAAAAA    450

D245      AAGGTAATAACAACCTTCAAGAGCCCCTTCATCTCAACTCGGCATAAACAAGGCAAGATTCTGAGAGTGGCCGCC    525

D245      CCTGGAAGCAGAAATTATTCTTGTGGCTATCCATTGGCTCCTGAGGCTCTAATCAGAGATGGGGCACCTTTAGTA    600

D245      CCAGGGGAGTGACTGTTGCCCATAAGGTACTGGACATCAACTTTCAAGAGCAGCCCCAGCTCCTTAAGCTGCTGG    675

D245      TCCTGGTGCATCTGCTGACTTTCATGTAGAAGATAGCAGAGCTTTGGCGACATTACAACATAAGAACTGCAGAGA    750

D245      GGTGTAATCCCAGTGGAAGACTGAATCGAGAGACTCAAAAAGGAAGTTATGCCTTCTCAGAATGCTGTTTTTTCT    825

D245      CAGGAGGGGAACATGGAGGAGGAAGAAATGAATGATGGCTCACAGATGGTGAGATCTCAGTGAGCCAAGGGAGTT    900
                                                                 ::::::::::::::::
EGFR                                         ...GGACAAGTGCAAGCTTCTGGAGGGTGAGCCAAGGGAGTT   1832

D245      TGTGGAGAACTCTGAGTGCATACAGTGCCACCCAGAGTGCCTGCCTCAGGCCATGAACATCACCTGCACAGGACG    975
          ::::::::::::::::::::::::::::::::::::::::::::::::::::::::::::::::::::::::::
EGFR      TGTGGAGAACTCTGAGTGCATACAGTGCCACCCAGAGTGCCTGCCTCAGGCCATGAACATCACCTGCACAGGACG   1907
D245AA                                                           M  N  I  T  C  T  G  R

D245      GGGACCAGACAACTGTATCCAGTGTGCCCACTACATTGACGGCCCCCACTGCGTCAAG...               1033
          ::::::::::::::::::::::::::::::::::::::::::::::::::::::::::
EGFR      GGGACCAGACAACTGTATCCAGTGTGCCCACTACATTGACGGCCCCCACTGCGTCAAG...               1965
D245AA     G  P  D  N  C  I  Q  C  A  H  Y  I  D  G  P  H  C  V  K ...
v-erb B    G  P  D  N  C  M  K  C  A  H  F  I  D  G  P  H  C  V  K ...
```

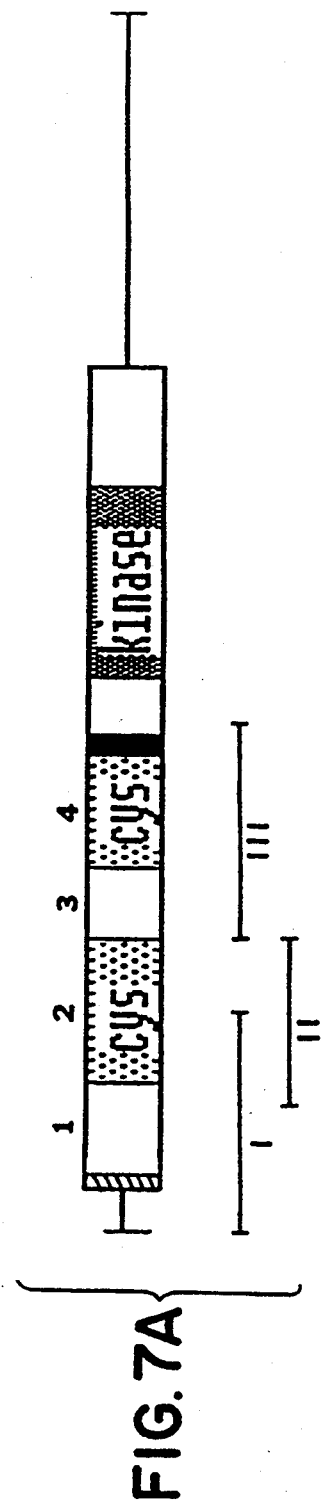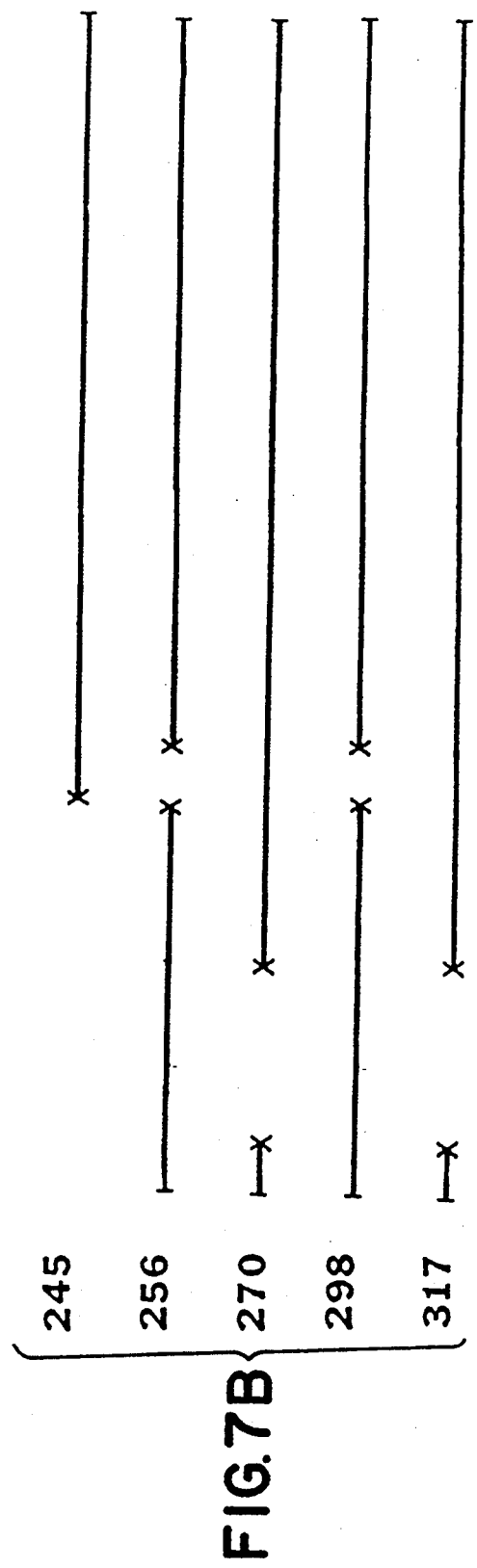
FIG.7A
FIG.7B

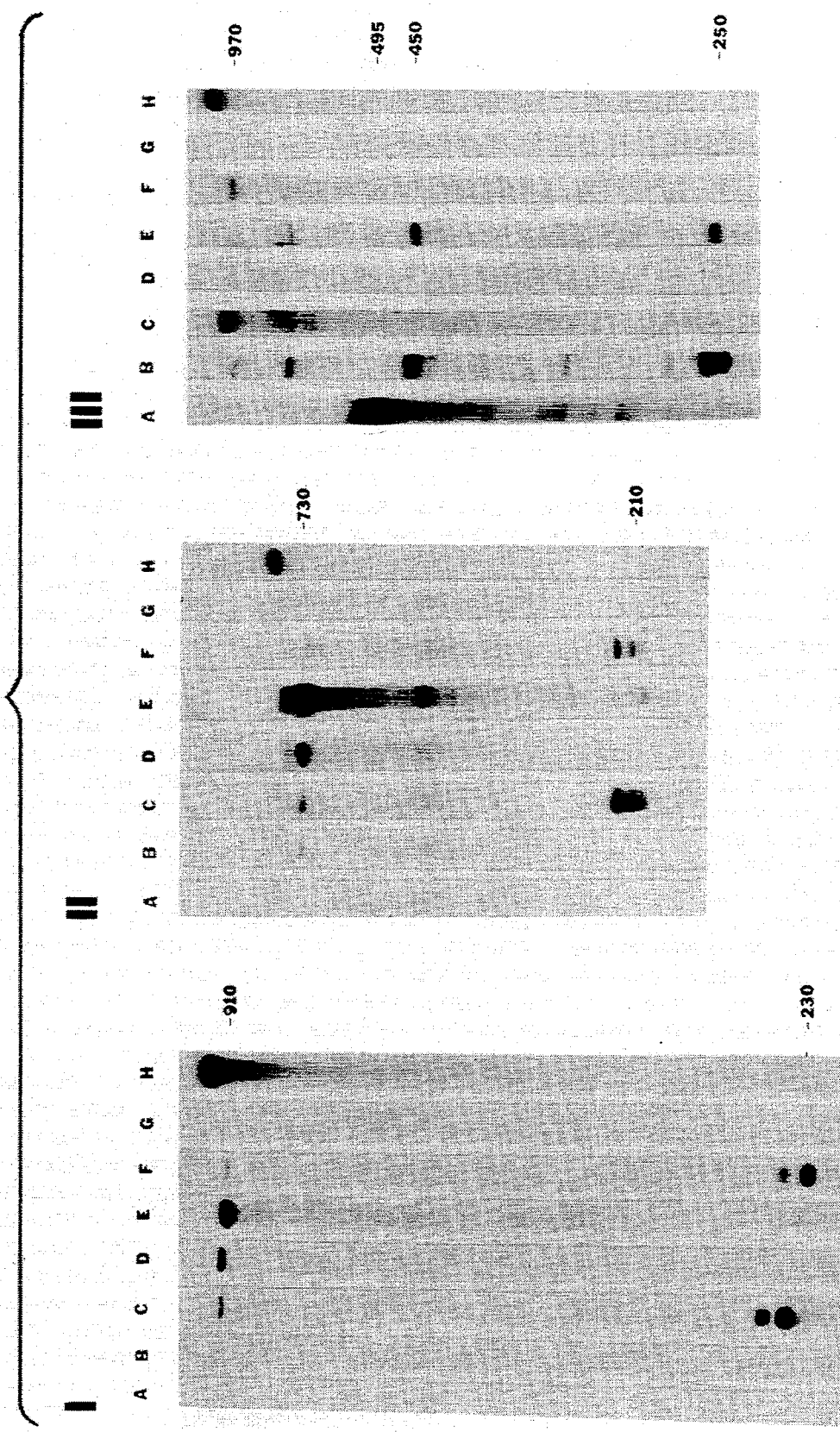

```
Leu Glu Glu Lys Val Cys Gln ... Lys Cys Pro Arg Asn Tyr Val
CTG GAG GAA AAG GTT TGC CAA ... AAG TGT CCC CGT AAT TAT GTG
                        274*                          *1076

Leu Glu Glu Lys Lys Gly Asn Tyr Val Val Thr
            CTG GAG GAA AAG AAA GGT AAT TAT GTG GTG ACA
```

FIG. 8B

```
Cys Asn Leu Leu Glu Gly Glu Pro ... Thr Tyr Gly Cys Thr Gly Pro
TGC AAG CTT CTG GAG GGT GAG CCA ... ACC TAC GGA TGC ACT GGG CCA
                        1817*                          *2067

Gly Cys Thr Gly Pro Gly
            GGA TGC ACT GGG CCA GGT
```

FIG. 8C

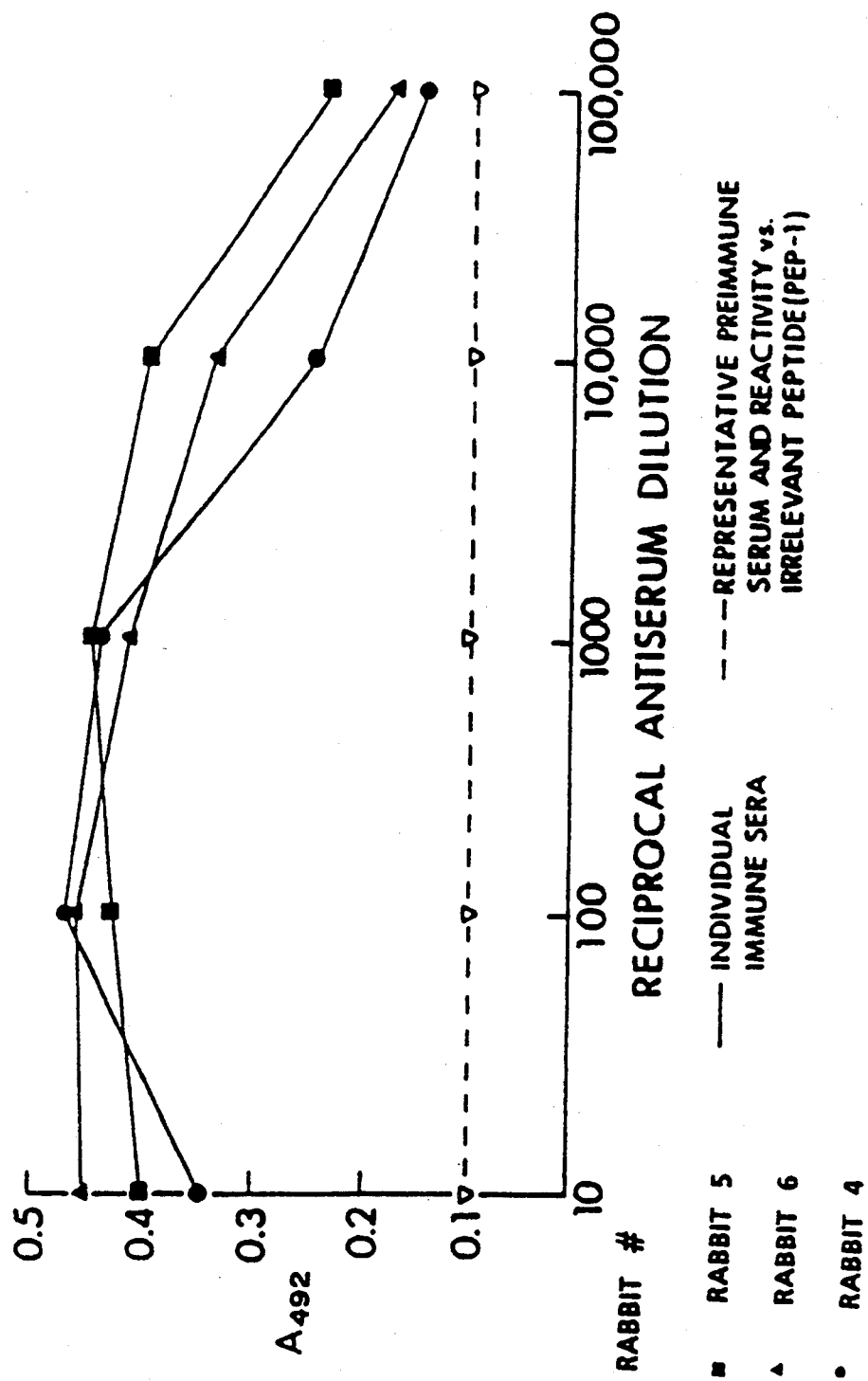

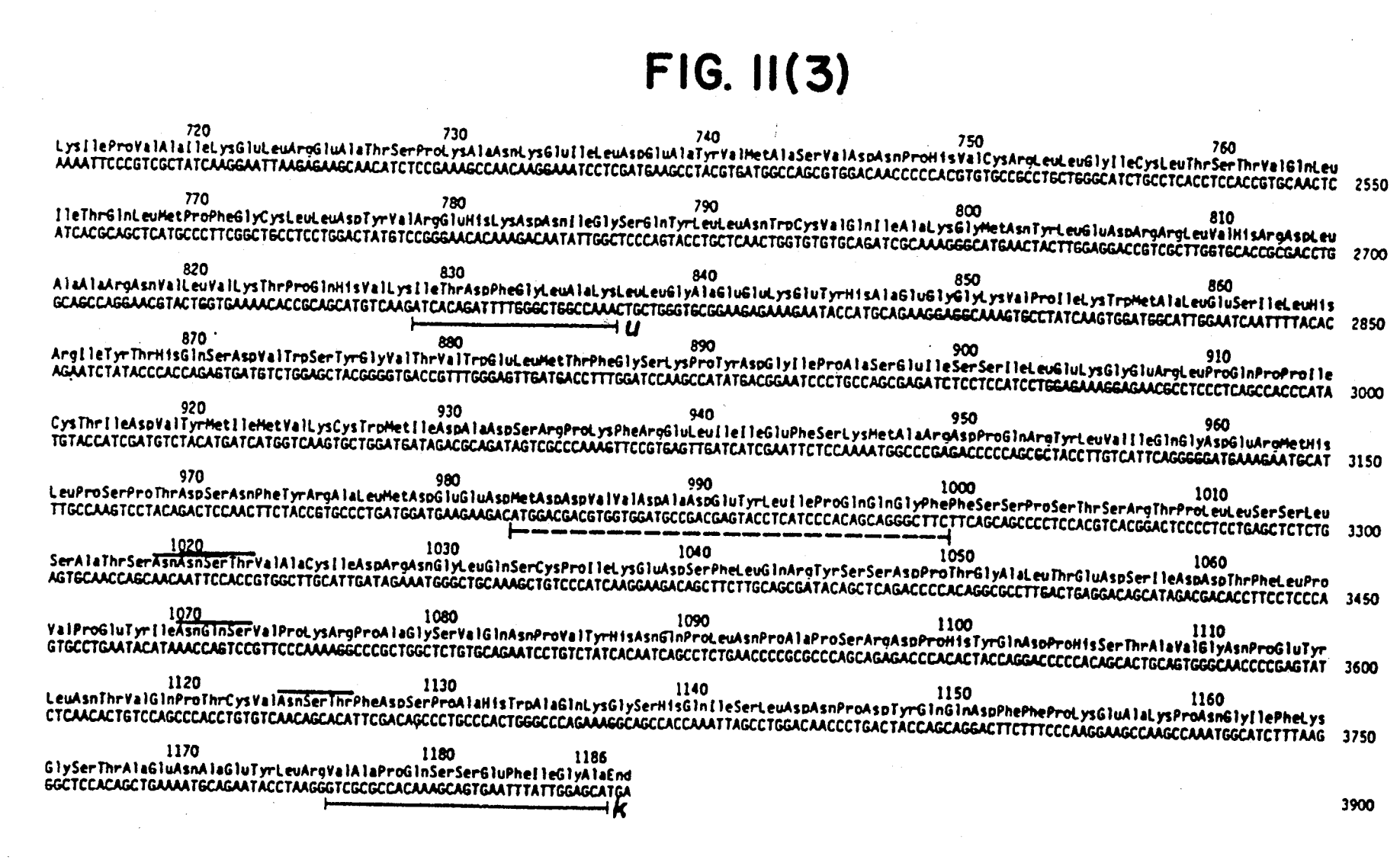

STRUCTURAL ALTERATIONS OF THE EGF RECEPTOR GENE IN HUMAN GLIOMAS

This invention was made with the support of the National Institutes of Health. The United States Government retains certain rights in the invention.

This application is a division of application Ser. No. 07/627,869, filed Dec. 17, 1990, now U.S. Pat. No. 5,212,290, which is a divisional of Ser. No. 07/531,410, filed Jun. 1, 1990, now abandoned; which is a CIP of Ser. No. 07/404,226, filed Sep. 8, 1989, now abandoned.

FIELD OF THE INVENTION

The invention relates to tumors and carcinoma involving mutations of the epidermal growth factor receptor (EGFR).

BACKGROUND OF THE TECHNOLOGY

Tumor specific molecules to aid in better diagnosis and treatment of human and animal cancer have been sought since the last century. Hard evidence of tumor-specific substances, based on molecular structural data, has been difficult to provide in most types of human cancer except those based on vitally-induced cancer and involving molecular structures specified by the virus genome. There have been extremely few examples of tumor-specific molecules based on novel molecular structures. In the case of malignant human gliomas and other tumors potentially associated with amplification or changes in the epidermal growth factor receptor molecule, such as carcinoma of the breast and other human carcinomas, there have been no unequivocal demonstrations of structurally altered molecules with unique sequences.

The epidermal growth factor receptor (EGFR) is the 170 kilodalton membrane glycoprotein product of the proto-oncogene c-erb B. The sequence of the EGFR gene is known (Ullrich et al., 1984). The EGFR gene is the cellular homolog of the erb B oncogene originally identified in avian erythroblastasis viruses (Downward et al., 1984; Ullrich, et al. 1984). Activation of this oncogene by gene amplification has been observed in a variety of human tumors (Haley et al., 1987a), and in particular, those of glial origin (Libermann et al., 1985; Wong et al., 1987; Yamazaki et al., 1988; Malden et al., 1988).

One major difference between v-erb B oncogenes and the normal EGFR gene is that the vital oncogenes are amino-truncated versions of the normal receptor; they lack most of the extracytoplasmic domain but retain the transmembrane and tyrosine kinase domains (Fung et al., 1984; Yamamoto et al., 1983, Nilsen et al., 1985; Gammett et al., 1986). This results in a protein that is unable to bind epidermal growth factor (EGF) but can still phosphorylate other substrates (Gilmore et al., 1985; Kris et al., 1985), and has led to speculation that the v-erb B proteins are oncogenic because the kinase domain is unregulated and constitutively active (Downward et al., 1984).

A variety of genetic alterations can occur in viral erb B oncogenes, e.g. amino acid substitutions and deletions in the carboxy terminus of the gene. Available evidence, however, argues that the amino truncation is critical to carcinogenesis. Amino truncations are a feature of all v-erb B oncogenes, including those that arise by promoter insertion or retrovital transduction (Nilsen et al., 1985; Gammett et al., 1986).

In contrast, carboxy-terminal deletions appear to be associated only with tumors that arise through retroviral transduction and seem to determine host range and tumor type specificity (Gammett et al., 1986; Raines et al., 1985). Transfection experiments with amino-truncated avian c-erb B genes or chimeric viral oncogene-human EGF receptors demonstrates that this deletion is sufficient alone to create a transforming protein (Pelley et al., 1988; Wells et al., 1988).

Amplification of the EGFR gene occurs in 40% of malignant human gliomas (Libermann et al., 1985; Wong et al., 1987). Rearrangement of the receptor gene is evident in many of the tumors with gene amplification. The structural alterations seem to preferentially affect the amino terminal half of the gene (Yamazaki et al., 1988; Malden et al., 1988), but the nature of the rearrangements has not been precisely characterized in any tumor.

Size variant EGFR genes and amplification have been reported in several human cancers. (Humphrey et al., 1988; Bigner et al., 1988; Wong et al., 1987; and Humphrey et al., 1989) There has been no determination, however, of the molecular basis for the altered EGFR molecules in cells. A determination of the genetic changes responsible for these tumors would present a significant step forward in the treatment and diagnosis of human carcinoma.

It would be desirable to have unique gene and peptide sequences for glioma EGFR. It would also be desirable to have a synthetic peptide against which monoclonal or polyclonal antibodies could be produced which demonstrate specificity against mutant EGFR.

Bibliography

Alitalo, K. (1984). Amplification of Cellular Oncogenes in Cancel Cells. Medical Biology 62:304–317.

Bartels, I., Grzeschik, K. H., Cooper, D. N., Schmidtke, J. (1986). Regional Mapping of Six Cloned DNA Sequences on Human Chromosome 7. Am. J. Hum. Genet. 3:280–287.

Bigner, S. H., Mark, J., Bullard, D. E., Mahaley, Jr., M. S., Bigner, D. D. (1986). Chromosomal Evolution in Malignant Human Gliomas Start with Specific and Usually Numerical Deviations. Cancer Genet. Cytogenetics 22:121–135.

Bigner et al., J. Neuropathol. Exp. Neurol., 47:191–205 (1988);

Bullard et al. (1986). In Vivo Imaging of Intracranial Human Glioma Xenografts Comparing Specific with Nonspecific Radiolabeled Monoclonal Antibodies. J. Neurosurg. 64:257–262

Carpenter, G. (1987). Receptors for Epidermal Growth Factor and Other Polypeptide Mitogens. Annual Review of Biochemistry 56:991–914.

Carrasquillo, et al., Cancer Treat. Rep., 68:317–328 (1984), "Diagnosis of and Therapy for Solid Tumors With Radiolabeled Antibodies and Immune Fragments".

Chomczynski, P., Sacchi, N. (1987). Single-step Method of RNA Isolation by Acid Guanidinium Thiocyanate-Phenol-Chloroform Extraction. Anal. Biochem 162:156–159.

Deininger, P. L. Jolly, D. J., Rubin, C. M., Friedman, T., Schmid, C. W. (1981). Base Sequence Studies of 300 Nucleotide Renatured Repeated Human DNA Clones. Journal of Molecular Biology 151: 17–33.

Di Fiore, P. P., Pierce, J. H., Fleming, T. P., Hazan, R., Ullrich, A., King, C. R., Schlessinger, J., Aaronson, S. A. (1987). Overexpression of the Human EGF Receptor Confers an EGF-Dependent Transformed Pheotype to NIH 3T3 Cells. Cell 51:1063–1070.

Downward, J., Yarden, Y., Mayes, E., Scarce, G., Totty, N., Stockwell, P., Ullrich, A., Schlessinger, J., Waterfield, M. D. (1984). Close Similarity of Epidermal Growth Factor Receptor and v-erb B Oncogene Protein Sequence. Nature 307:521–527.

European Patent Application 0 153 114 (1985)

Feinberg, A. P., Vogelstein, B. (1984). A Technique for Radiolabeling DNA Restriction Endonuclease Fragments to High Specific Activity. Anal. Biochem. 137:266–267.

Fung, Y. K., Lewis, W. G., Crittenden, L. B., Kung, H. J. (1984). Activation of the Cellular Oncogene c-erb B by LTR Insertion: Molecular Basis for Induction of Erythroblastosis by Avian Leukosis Virus. Cell 33:357–368.

Gammett, D. C., Tracy, S. E., Robinson, H. L., (1986). Differences in Sequences Encoding the Carboxy-Terminal Domain of the Epidermal Growth Factor Receptor Correlate with Differences in the Disease Potential of Viral erbB Genes. Proc. Natl. Acad. Sci. U.S.A. 83:6053–6057.

Gilmore, T., DeClue, J. E., Martin, G. S. (1985). Protein Phosphorlytion at Tyrosine is Induced by the v-erb B Gene Product in Vivo and In Vitro. Cell 40:609–618.

Gubler, U., Hoffman, B. J., (1983). A Simple and Very Efficient Method for Generating cDNA Libraries. Gene 25:263–269.

Haley, J. D., Kinchington, D., Whittloe, N., Waterfield, M. D., Ullrich, A. (1987A). The Epidermal Growth Factor Receptor Gene in: Oncogenes, Genes, and Growth Factors Edited by: Guroff, G. 12th Edition. Chapter 2. pp. 40–76. Wiley, New York.

Haley, J., Whittle, N., Bennett, P., Kinchington, D., Ullrich, A., Waterfield, M. (1987b). The Human EGF Receptor Gene: Structure of the 110 kb Locus and Identification of Sequences Regulation its Transcription. Oncogene Research 1:375–396.

Haley, J. D., Hsuan, J. J., and Waterfield, M. D. (1989). Analysis of Mammalian Fibroblast Transformation by Normal and Mutated Human EGF Receptors. Oncogene 4:273–283.

Henikof, S. (1984). Unidirectional Digestion with Exonuclease III Creates Targeted Breakpoints for DNA Sequencing. Gene 29:351–359.

Humphrey, P. A., Wong, A. J., Vogelstein, B., Friedman, H. S., Wernerr, M. H., Bigner, D. D., Bigner, S. H. (1988). Amplification and Expression of the Epidermal Growth Factor Receptor Gene in Human Glioma Xenografts. Cancer Research 48:2231–2238.

Humphrey et al., J. Neurooncol. (1989)

Hyrien, O., Debatisse, M., Buttin, G., de, Saint, Vincent, B. R. (1987). A Hotspot for Novel Amplification Joints in a Mosaic of Alu-like Repeats and Palindromie A+T-rich DNA. EMBO. J. 6:2401–2408.

Janson, C. H., Tehrani, M. J., Mellstedt, H., and Wigzell, H. (1989). Anti-idiotypic Monoclonal Antibody to a T-cell Chronic Lymphatic Leukemia. Cancer Immunology Immunotherapy 28:22–232.

Kawasaki, E. S., Clark, S. S., Coyne, M. Y., Smith, S. D., Champlin, R., Witte, O. N., McCormick, F. P. (1988). Diagnosis of Chronic Myeloid and Acute Lymphocytic Leukemias by Detection of Leukemia-Specific DNA mRNA Sequences Amplified in Vitro. Proc. Natl. Acad. Sci. U.S.A. 85:5698–5702.

Kozak, M. (1987). An Analysis of 5'-Noncoding Sequences from 699 Vertebrate Messenger RNAs. Nucleic. Acids. Res. 15:8125–8148.

Kris. R. M., Lax, I., Gullick, W., Waterfield, M. D., Ullrich, A., Fridkin, M., Schlessinger, J. (1985). Antibodies Against a Synthetic Peptide as a Probe for the Kinase Activity of the Avian EGF Receptor and v-erB Protein. Cell 40:619–625.

Lax, I., Brugess, W. H., Bellot, F., Ullrich, A., Schlessinger, J., Givol, D. (1988). Localization of a Major Receptor Binding Domain in the Epidermal Growth Factor by Affinity Labelling. Molecular and Cellular Biology 8:1831–1834.

Lee et al. (1988). Therapeutic Efficacy of Antiglioma Mesenchymal Extracellular Matrix $^{131}$I-Radiolabeled Murine Monoclonal Antibody in a Human Glioma Xenograft Model. Cancer Research 48:539–566

Lehrman, M. A., Schneider, W. J., Sudhof, T. C., Brown, M. S., Goldstein, J. L., Russell, D. W. (1985). Mutation in LDL Receptor: Alu-Alu Recombination Deletes Exons Encoding Transmembrane and Cytoplasmic Domains. Science 227:140–146.

Libermann, T. A., Nusbaum, H. R., Razon, N., Kris, R., Lax, I., Soreq, H., Whittle, N., Waterfield, M. D., Ullrich, A., Schlessinger, J. (1985). Amplification, Enhanced Expression and Possible Rearrangement of EGF Receptor Gene in Primary Human Brain Tumours of Glial Origin. Nature 313:144–147.

Malden, L. T., Novak, U., Kaye, A. H., Burgess, A. W. (1988). Selective Amplification of the Cytoplasmic Domain of the Epidermal Growth Factor Receptor Gene in Glioblastoma Multiforme. Cancer Research 48:2711–2714.

Meeker, et al., Blood, 65:1349–1363 (1985), "A Clinical Trial of Anti-Idiotype Therapy for B Cell Malignancy".

Merlino, G. T., Ishii, S., Whang, P. J., Knutsen, T., Xu, Y. H., Clark, A. J., Stratton, R. H., Wilson, R. K., Ma, D. P., Roe, B. A. et al. (1985). Structure and Localization of Genes Encoding Aberrant and Normal Epidermal Growth Factor Receptor RNAs from A431 Human Carcinoma Cells. Molecular Cellular Biology 5:1722–1734.

Nilsen, T. W., Maroney, P. A., Goodwin, R., Rottman, R. M., Crittenden, L. B., Raines, M. A. Kung, H. J. (1985). c-erbB Activation in ALV-Induced Erythroblastosis: Novel RNA Processing and Promoter Insertion Results in Expression of an Amino-Truncated EGF Receptor. Cell 41:719–726.

Nister, M., Libermann, T. A., Betsholtz, C., Petterrson, M., Claesson-Welsh, L., Heldin, C-H., Schlessinger, J., Westermark, B. (1988). Expression of Messenger RNA's from Platelet-Derived Growth Factor and Transforming Growth Factor a and their Receptors in Human Malignant Glioma Cells. Cancer Research 48:3910–3918.

Pelley, R. J., Moscovici, C., Hughes, S., Kung, H. J. (1988). Proviral-Activated c-erbB is Leukemogenic but not Sarcomagenic: Characterization of a Replication-Competent Retrovirus Containing the Activated c-erbB. Journal of Virology 62:1840–1844.

Raines, M. A., Lewis, W. G., Crittenden, L. B., Kung, H. J. (1985). c-erbB Activation in Avian Leukosis Virus-Induced Erythroblastosis: Clustered Integration Sites and the Arrangement of Provirus in the c-erbB Alleles. Proc. Natl. Acad. Sci. U.S.A. 82:2287–2291.

Reed, K. C., Mann, D. A. (1985). Rapid Transfer of DNA from Agarose Gels to Nylon Membranes. Nucleic Acids Research 13:7207–7221.

Riedel, H., Massoglia, S., Schlessinger, J., Ullrich, A. (1988). Ligand Activation of Overexpressed Epidermal Growth Factor Receptors Transforms NIH 3T3 Mouse Fibroblasts. Proc. Natl. Acad. Sci. U.S.A. 85:1477-1481.

Ruppert, J. M., Kinzler, K. W., Wong, A. J., Bigner, S. H., Kao, F. T., Law, M. L., Seuanez, H. B., O'Brien, S. J., Vogelstein, B. (1988). The GLI-Kruppel Family of Human Genes. Molecular and Cellular Biology 8:3104-3113.

Russel, M., Kidd, S., Kelly, M. R. (1986). An Improved Filamentous Helper Phage for Generating Single-Stranded Plasmid DNA. Gene 45:333-338.

Sealey, P. G., Whittaker, P. A., Southern, E. M. (1985). Removal of Repeated Sequences from Hybridization Probes. Nucleic Acids Res. 13:1905-1922.

Sears, et al., The Lancet, Apr. 3, 1982, pp. 762-765, (1982) "Phase-I Clinical Trial of Monoclonal Antibody in Treatment of Gastrointestinal Tumours".

Sears, et al., J. Biol. Resp. Mod., 3:138-150 (1984), "Effects of Monoclonal Antibody Immunotherapy on Patients With Gastrointestinal Adenocarcinoma".

Sears, et al., Cancer Res., 45:5910-5913 (1985), "Phase II Clinical Trial of a Murine Monoclonal Antibody Cytotoxic for Gastrointestinal Adenocarcinoma."

Steck, P. A., Lee, P., Hung, M. C., Yung, W. K. A. (1988). Express of an Altered Epidermal Growth Factor Receptor by Human Glioblastoma Cells. Cancer Research 48:5433-5439.

Ullrich, A., Coussens, L., Hayflick, J. S., Dull, T. J., Gray, A., Tam, A. W., Lee, J., Yarden, Y., Libermann, T. A., Schlessinger, J., et al. (1984). Human Epidermal Growth Factor Receptor cDNA Sequence and Aberrant Expression of the Amplified Gene in A431 Epidermoid Carcinoma Cells. Nature 309:418-425.

Velu, T. J., Beguinot, L., Vass, W. C., Willingham, M. C., Merlino, G. T., Pastan, I., Lowry, D. R. (1987). Epidermal Growth Factor Dependent Transformation by a Human EGF Receptor Proto-Oncogene. Science 238:1408-1410.

Vogelstein, B., Fearon, E. R., Hamilton, S. R., Prelsinger, A. C., Willard, H. F., Michelson, A. M., Riggs, A. D., Orkin, S. H. (1987). Clonal Analysis Using Recombinant DNA Probes from the X-Chromosome. Cancer Research 47:4806-4813.

Vogelstein, B. (1987). Rapid Purification of DNA from Agarose Gels by Centrifugation through a Disposable Plastic Column. Anal. Biochem. 160:115-118.

Wells, A., Bishop, J. M. (1988). Genetic Determinants of Neoplastic Transformation by the Retroviral Oncogene v-erbB. Proc. Natl. Acad. Sci. U.S.A. 85:7597-7601.

Winship, P. R. (1989). An Improved Method for Directly Sequencing PCR Amplified Material using Dimethyl Sulphoxide. Nucleic Acids Research 17:1266.

Winter, E., Yamamoto, F., Almoguera, C., Perucho, M. (1985). A Method to Detect and Characterize Point Mutations in Transcribed Genes: Amplification and Overexpression of the Mutant c-Ki-ras Allele in Human Tumor Cells. Proc. Natl. Acad. Sci. U.S.A. 82:7575-7579.

Wong, A. J., Bigner, S. H., Bigner, D. D., Kinzler, K. W., Hamilton, S. R., Vogelstein, B. (1987). Increased Expression of the Epidermal Growth Factor Receptor Gene in Malignant Gliomas is Invariably Associated with Gene Amplification. Proc. Natl. Acad. Sci. U.S.A. 84:6899-6903.

Xu, Y. H., Ishii, S., Clark, A. J., Sullivan, M., Wilson, R. K., Ma, D. P., Roe, B. A., Merlino, G. T., Pastan, I. (1984). Human Epidermal Growth Factor Receptor cDNA is Homologous to a Variety of RNAs Overproduced in A431 Carcinoma Cells. Nature 309:806-810.

Yamamoto, G., Hihara, H., Nishida, T., Kawai, S., Toyashima, K. (1983). A New Avian Erythroblastosis Virus, AEV-H Carries erbB Gene Responsible for the Induction of Both Erythroblastosis and Sarcoma. Cell 34:225-232.

Yamazaki, H., Fukui, Y., Ueyama, Y., Tamaoki, N., Kawamoto, T., Taniguchi, S., Shibuya, M. (1988). Amplification of the Structurally and Functionally Altered Epidermal Growth Factor Receptor Gene (c-erbB) in Human Brain Tumors. Molecular and Cellular Biology 8:1816-1820.

Zengerling, S., Tsui, L. C., Grzeschik, K. H., Olek, K., Riordan, J. R., Buchwald, M. (1987). Mapping of DNA Markers Linked to the Cystic Fibrosis Locus on the Long Arm of Chromosome 7 [Published Erratum Appears in Am J Hum Genet 1987 Aug:41(2):330] Am. J. Hum. Genet. 40:228-236.

SUMMARY OF THE INVENTION

It is an object of the invention to provide intron free DNA molecules and peptides that correspond to mutant EGFR proteins.

It is another object of the invention to provide antibodies specific for mutant EGFR molecules that exhibit little or no cross-reactivity with normal human EGFR or other tissues.

It is a further object of the invention to provide diagnostic methods for the detection of gliomas.

It is an additional object of the invention to provide methods for the treatment of gliomas.

In accordance with these and other objects, one aspect of the invention contemplates an intron-free DNA molecule which encodes an EGFR mutant type I, II or III peptide.

In another aspect, the invention contemplates substantially pure EGFR mutant types I, II or III peptides. The invention also contemplates antibodies which specifically react with the EGFR mutants but which do not cross-react with normal, intact EGFR. Still further aspects of the invention relate to the diagnosis of glioma by determining the presence of the mutant EGFR proteins or the genes coding for them.

In yet another aspect, the invention contemplates the treatment of gliomas employing an antibody which is specific for EGFR mutant type I, II or III peptides.

The invention provides an important step forward in the diagnosis and treatment of tumors associated with altered EGFR genes. These tumors have previously been characterized by the presence of amplified EGFR genes. The present discovery is based on the existence of specific deletions/rearrangements in these amplified genes. These altered genes produce mutant EGFR proteins that can be identified by specific antibodies. A variety of materials attached to the antibodies allows highly specific diagnosis and treatment of tumors bearing these deletion/rearrangement sequences.

BRIEF DESCRIPTION OF THE DRAWINGS

FIG. 1 is an illustration of a mutant type I EGFR peptide and a nucleic acid sequence therefor.

FIG. 2 is an illustration of a mutant type II EGFR peptide and a nucleic acid sequence therefor.

FIG. 3 is an illustration of a mutant type III EGFR peptide and a nucleic acid sequence therefor.

FIG. 4A shows an EcoRI map of the human EGFR gene; FIG. 4B shows the structures of mutant EGFR Types I-III genes.

FIGS. 5A-5E characterize the rearranged fragment of a Type III mutant EGFR gene.

FIG. 6 characterizes a Type III mutant EGFR transcript.

FIGS. 7A-7C show transcript analysis by RNase protection.

FIGS. 8A-8C are analysis results of the gene products from mutant Types I-III.

FIGS. 9 and 10 describe polyclonal antibodies raised against a Type II mutant EGFR peptide. FIG. 9 shows the reactivity of antisera from three rabbits with fusion junction peptide in an ELISA assay. Free peptide was bound to polyvinyl chloride plates. FIG. 10, left, shows immunoprecipitation of mutant EGFR protein but not intact EGFR by anti-peptide 2 antibody. On the right, immunoprecipitation by monoclonal antibody 528 of EGFR from A431-X, D-256 MG-X and D-270MG-X is shown.

FIG. 11 is the cDNA sequence of normal EGFR.

DETAILED DESCRIPTION OF THE INVENTION

Figure 4C:
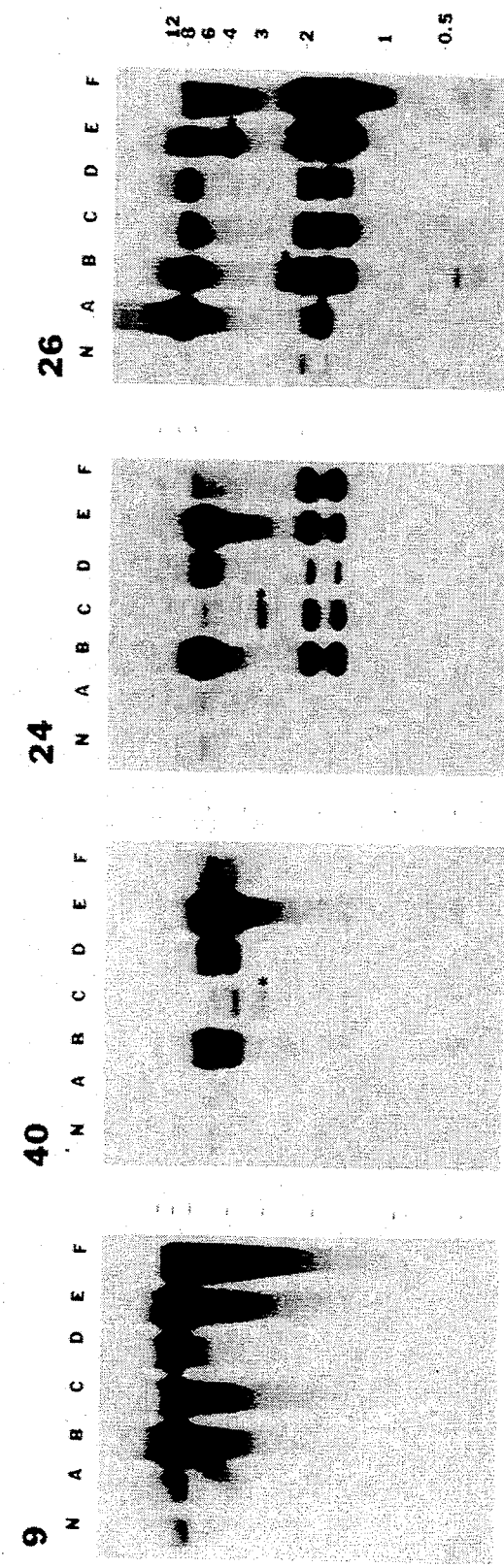
FIG. 4C shows Southern blot hybridization results.

One of the unexpected discoveries of this invention is that identical deletions (at the gene product level) were observed in tumors arising in different patients. Previous studies with glioma xenografts have shown that protein expressed from the amplified EGFR gene is on the cell surface (Humphrey et al., 1988). It is a finding of the present invention that there are amino acids present at some deletion junctions which are not present on normal cells. Thus, there are surface molecules in these tumors against which tumor-specific antibodies can be generated. Such tumor-specific antibodies can be used to diagnose and treat these widespread gliomas. (See, for example, Janson et al. (1989) regarding the use of antibodies in the treatment of lymphoid leukemias.)

Mutant EGFR protein is present in cells exhibiting one or more of three types of genetic deletion and/or rearrangement which result in a structurally altered receptor. The mutations resulting in these three types of altered receptor are illustrated in FIGS. 1-3. The first class of deletions (Type I, FIG. 1) results in a gap in the extracytoplasmic domain near the transmembrane domain. The second type of deletion (Type II, FIG. 2) results in the elimination of the distal portion of the extracytoplasmic domain of EGFR. The Type I and II in-frame deletions produce two new junction points in the amino acid sequence. A third type of abnormality (Type III, FIG. 3) is characterized by a deletion of the majority of the external domain of the EGFR leaving substantially only the transmembrane portion and the intracytoplasmic domain.

Type III mutations leave little or no extracellular protein. Although antibodies may detect an extracellular sequence, it is preferable to solubilize a cell with a Type III mutation in a detergent before exposure to antibodies.

The cDNA sequence corresponding to normal EGFR has been reported by Ulrich, et al., in Nature, 309:418-425 (1984). (FIG. 11) Intron-free DNA sequences encoding deletion mutant EGFR Types I, II and III can be determined from the information provided in FIGS. 1, 2 and 3 respectively, in view of the previously disclosed sequence for the normal receptor. In particular, a gene encoding deletion mutant EGFR Type I contains DNA segments corresponding to base numbers 1817 and 2067 of the normal sequence connected together as shown in FIG. 1 with the segment corresponding to base numbers 1818-2066 deleted. A gene encoding deletion mutant EGFR Type II contains DNA segments corresponding to base numbers 1-274 and 1076 to end of the normal sequence connected together as shown in FIG. 2 with the segment corresponding to base numbers 275-1075 deleted. A gene encoding deletion mutant EGFR Type III contains a DNA segment corresponding to base numbers 1817 to the end with the segment corresponding to base numbers 1-1816 deleted. Other DNA sequences which encode the same amino acid sequences may be used to generate EGFR mutant peptides in recombinant organisms, due to the degeneracy of the genetic code. Intron-free DNA molecules may be obtained using reverse transcriptase, for example, and an EGFR mRNA as a template. Alternatively, the DNA molecules can be chemically synthesized according to the sequences disclosed herein. Such molecules can be amplified using polymerase chain reaction (PCR) to facilitate analysis and manipulations.

The DNA sequences and DNA molecules of the present invention may be introduced into a host cell by transformation or transfection (to create transformed cells) and expressed using a wide variety of host/vector combinations. For example, useful vectors may comprise segments of chromosomal, non-chromosomal (such as various known derivatives of SV40 and known bacterial plasmids, e.g., plasmids from *E. coli* including colE1, pcR1 pBR322, pMB9 and RP4), or synthetic DNA sequences, phage DNAs (M13) including derivatives of phage (e.g., NM 989) and filamentous single-stranded DNA phages, vectors useful in yeasts (such as the 2 u plasmid), vectors useful in eukaryotic cells (such as vectors useful in animal cells, e.g. those containing SV-40 adenovirus and retrovirus derived DNA sequences) and vectors derived from combinations of plasmids and phage DNAs (such as plasmids which have been modified to employ phage DNA), or other derivatives thereof.

Such expression vectors are also characterized by at least one expression control sequence that may be operatively linked to the mutant EGFR DNA sequence inserted in the vector to control and regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast (e.g., the promoter for 3-phosphoglycerate kinase), the promoters of yeast acid phosphatase (e.g., Pho5), the promoters of the yeast a-mating factors, and promoters derived from polyoma, adenovirus, retrovirus, or simian virus (e.g., the early and late promoters of SV40), and other sequences known to control the expression of genes of prokaryotic or eukaryotic cells and their viruses or combinations thereof.

Furthermore, within each specific expression vector, various sites may be selected for insertion of the DNA sequences of this invention. These sites are usually designated by the restriction endonuclease which cuts them. They are well recognized by those of skill in the art. It is, of course, to be understood that an expression vector useful in this invention need not have a restriction endonuclease site for insertion of the chosen DNA fragment. Instead, the vector can be joined to the fragment by alternative means. The host cell, expression vector, and in particular the site chosen therein for insertion of a selected DNA fragment and its operative linking therein to an expression control sequence, is determined by a variety of factors, e.g., number of sites susceptible to a particular restriction enzyme, size of the protein and its susceptibility to proteolytic degradation by host cell enzymes, contamination or binding of the protein to be expressed by host cell proteins difficult to remove during purification; expression characteristics, such as the location of start and stop codons relative to the vector and an insertion site for a DNA sequence is determined by a balance of these factors, not all selections being equally effective for a given case.

Useful expression hosts may include well known eukaryotic and prokaryotic hosts, such as strains of *E. coli*, such as *E. coli* SG-936, *E. coli* HB 101, *E. coli* W3110, *E. coli* X1776, *E. coli* X2282, *E. coli* DHI, and *E. coli* MRC1, Pseudomonas, Bacillus, such as *Bacillus subtilis*, Streptomyces, yeasts and other fungi, animal cells, such as COS cells and CHO cells, and human cells and plant cells in tissue culture.

Of course, not all host/expression vector combinations function with equal efficiency in expressing the DNA sequences of this invention or in producing the polypeptides of this invention. However, a particular selection of a host/expression vector combination may be made by those skilled in the art. For example, the selection should be based on a balancing of a number of factors. These include compatibility of the host and vector, toxicity of the proteins encoded by the DNA sequence to the host, ease of recovery of the desired protein, expression characteristics of the DNA sequences and the expression control sequences operatively linked to them, biosafety, costs and the folding, form or any other necessary postexpression modifications of the desired protein.

One preferred means of obtaining the deletion mutant EGFR preparations of this invention is to synthesize them according to standard techniques known in the art using the sequences taught herein. Another means contemplates culturing cells transfected with an expression vector comprising an intron-free DNA molecule corresponding to FIG. 1 or FIG. 2 or FIG. 3 using culture conditions which are well-known in the art. The cells are then harvested and the cell membrane fraction may be separated by standard separation procedures, such as differential centrifugation, which are well-known in the art. A crude extract can be obtained by solubilizing the cell membrane fraction with detergents.

Once a crude extract containing the deletion mutant EGFR is obtained, purification can be accomplished according to techniques which are well-known in the protein purification art. For example, various types of chromatography may be used. Columns which may be used include a DEAE cellulose column, or an anion exchange column, as well as a gel permeation column.

The deletion mutant EGFR protein or peptide fragments thereof can also be purified using immunoaffinity techniques. As antibodies are provided here which are specific for the epitopes shown in FIGS. 1, 2, and 3, peptides corresponding to Type I, II, or III mutants can be positively selected from a mixture of many proteins. The use of the antibodies of the present invention to purify the proteins of the invention allows good separation from those proteins which are most similar to them. Alternatively, peptides of this invention may be purified by immunoaffinity using antibodies to the normal EGFR, especially to epitopes on the cytoplasmic domain. Of course, other techniques of purification are known in the art and can be used to purify the peptides of the invention.

Those of ordinary skill in the art can select among the above techniques to prepare the substantially pure peptides of this invention. Substantially pure mutant EGFR peptides within the contemplation of this invention are those which are substantially free of other human proteins. Peptides according to the present invention are linear polymers of amino acids which do not contain the full intact sequence of EGFR found in normal cells. Typically these are greater than ten amino acids in length and less than about fifty. Desirably the peptides are long enough to elicit a unique antibody response but short enough so that antibodies are not elicited which are immunoreactive with the intact EGFR protein.

The peptide product of the prokaryotic and eukaryotic hosts transformed with the DNA sequences of this invention, can be employed in the production of antibodies.

The substantially pure preparation of polypeptide comprising the amino acid sequence corresponding to the nucleotide sequences of FIGS. 1, 2 and 3 can be made using any of the techniques which are known in the art. For example, the Merrifield technique (Journal of American Chemical Society, vol. 85, pp. 2149-2154, 1968), can be used. Substantial purity means that the preparation is greater than 75% free of other proteins normally found in human cells. Preferably the preparation is greater than 90% free of other human proteins. Polypeptides may be longer or shorter or have conservative amino acid changes which do not change the epitope(s) found on deletion mutant EGFR but not found on normal intact EGFR. Polypeptides can be tested to determine if they are able to stimulate mammals to produce antibodies which are immunoreactive with epitopes found on deletion mutant EGFR, but not found on normal EGFR. Methods of immunizing mammals to stimulate antibody preduction are well known in the art. Methods for testing the immunoreactivity of antibodies for known antigens are also well known.

The substantially pure preparation of polypeptide of the present invention can be used to affinity purify antibodies specific for the deletion mutant EGFR protein. In addition, the preparation of polypeptide of the present invention can be used to stimulate production of antibodies in a mammal by immunizing the mammal with the preparation. Such immunization may optionally employ coupling of the polypeptide to a larger immunogenic substance such as keyhole limpet hemocyanin. For affinity purification of antibodies, the polypeptide can be coupled to an inert matrix, such as agarose beads. Techniques for such coupling are well known in the art. The preparation of the polypeptide can also be used to quantitate antibodies specific for deletion mutant EGFR in an antibody preparation. In such a case, the synthetic peptide will usually be coupled to a larger inert proteinaceous substance such as bovine serum albumin. Once again, the techniques for coupling polypeptides to such matrices are well known in the art.

As mentioned above, antibodies which are specific for the deletion mutant EGFR proteins in that they are immunoreactive with the deletion mutant EGFR protein but not with normal, intact EGFR can be made using a synthetic polypeptide of the present invention. Immunization of mammals such as rabbits, mice, goats, etc. to produce antibodies is well known in the art. Such polyclonal antibody preparations can be purified using immunoaffinity techniques employing a synthetic polypeptide of the present invention. Such purification methods are well-known in the art. Monoclonal antibodies can also be raised which are specific for deletion mutant EGFR epitopes and do not cross-react with normal EGFR. Generally, a rat or mouse will be immunized with the synthetic polypeptide (or deletion mutant protein) of the present invention and the rodent will later be sacrificed and spleen cells recovered for fusion with myeloma cells. Hybrid cells can be selected according to techniques known in the art, for example, selections involving complementation of two phenotypes, one from each parental cell. The antibody produced by each hybrid cell clone can be screened individually to select antibodies which bind to epitopes on deletion mutant EGFR but not on normal, intact EGFR.

In order to screen for antibodies which are immunoreactive with epitopes found on the deletion mutant EGFR gene product but not found on normal EGFR, a simple battery of tests can be performed. Antibodies can be tested for immunoreactivity with deletion mutant EGFR using a substantially pure preparation of the protein, or with fragments of the deletion mutant EGFR protein according to the present invention conjugated to a larger moiety such as bovine serum albumin. The desired specific antibodies should be positive in either or both of these tests. The antibodies should also be tested for immunoreactivity with normal, intact EGFR; desired antibodies having absolute specificity for deletion mutant EGFR should be negative in such tests.

Antibodies can also be detected using this battery of tests which have relative specificity for deletion mutant EGFR compared to normal EGFR. That is, some monoclonal antibodies can be found which react more strongly with the deletion mutant protein than with the normal protein. These antibodies of relative specificity for mutant EGFR may also be useful. Means for using them are discussed below.

Immunoaffinity techniques to purify monospecific polyclonal antibodies reactive with deletion mutant EGFR but not with normal EGFR can be used. Similar binding properties are employed as in the tests described for monoclonal antibodies above. That is to say that antibodies which immunoreact with deletion mutant EGFR will be positively selected, while those that immunoreact with normal EGFR will be removed from the desired antibody preparation.

Antibodies which show relative or preferential specificity for deletion mutant EGFR relative to normal EGFR can be rendered absolutely specific by altering the conditions under which immunoreactivity is assayed. Conditions in the assay medium which can be altered include, but are not limited to: the ionic strength; the detergent concentration; the concentration of chaotropic agents, such as urea, guanidine, and potassium thiocyanate; and the pH. Alteration of these conditions leads to destabilization of the various bonding forces which contribute to antibody-antigen binding. Titration of reagents altering each of these conditions allows determination of a set of conditions where relatively or preferentially specific antibodies immunoreact with deletion mutant EGFR but not with normal EGFR. Suitable ranges in which to vary the destabilizing agent concentrations can readily be determined. For example, in order to alter ionic strength, potassium chloride can be titrated from about 0.05M to 2M. Detergents, either ionic or non-ionic, can be titrated from about 0.05% to 2%. Chaotropic agents can be titrated from about 0.5M to 8M. The range of pH can be titrated from about 2 to 10. Such conditions can be useful both to screen for monoclonal antibodies immunoreactive with deletion mutant EGFR and to assay for deletion mutant EGFR in various biological sources.

Diagnostically, knowing the EGFR lesions correlated with tumors of Types I, II, and III permits the development of gene or antibody probes for accurately diagnosing and classifying tumors.

The nucleotide sequences provided by the invention can be used to form gene probes in accordance with any of the standard techniques. The DNA probes contemplated for use in this invention may be derived from the DNA of cell lines grown in vitro or xenografts maintained in vivo which contain the DNA spanning the deletion site. The size of a DNA probe can vary from approximately 20 nucleotides to hundreds of nucleotides. The DNA probe may be radiolabeled, labeled with a fluorescent material, or the like. Procedures for the preparation and labeling of DNA probes are well known in the art.

The diagnostic test employing a DNA probe will employ a cell sample from an individual who is being screened for the presence of glioma. The sample will be isolated from the suspect tissue. DNA is recovered from the cell employing standard techniques well known to those skilled in the art. The DNA is then incubated with a probe under conditions where homologous sequences hybridize but sequences which diverge do not, and hybridization is thereafter detected. Hybridization to a deletion-specific probe indicates the presence of the deletion. Enzymes such as S1 nuclease can be employed to remove portions of a DNA or RNA molecule which do not hybridize. The size of the duplex nucleic acid which remains can be determined by standard means. Duplexes which are smaller than the probe indicate a deletion, rearrangement, or other mismatch. Thus probes which are useful may be derived from intact as well as mutant alleles.

Antibodies of the invention are capable of binding to the mutant EGFR proteins and not to the intact EGFR protein from normal cells. These antibodies also permit the use of imaging analysis with isotopes, conjugated antibodies, or other ligands. Examples of suitable imaging agents are $^{125}I$, $^{123}I$, $^{131}I$, or Indium-111 conjugated to the antibodies specific for deletion mutants of the EGFR.

The antibodies of the present invention can be used to detect deletion mutant EGFR epitopes in histological sections of glioma tissue as well as in other solid tumors. Tissue samples are preferably solubilized with detergent to release membrane proteins into solution prior to immunological detection. One can detect antibody binding to extracts of tissue sections by any detection means known in the art for example, radioimmunoassay, enzyme-linked immunoadsorbent assay, complement fixation, nephelometric assay, immunodiffusion or immunoelectrophoretic assay. Alternatively, the antibodies can be used as an immunohistochemical reagents to visualize EGFR mutant proteins in tissue sections.

In addition, the antibodies of the invention can be administered to a patient for imaging analysis. For such purposes the antibodies are typically conjugated to an imaging agent, such as $^{123}$I, $^{131}$I, or Indium-111. A diagnostically effective amount of antibody is one which allows the observer to distinguish between normal tissues and those containing mutant type EGFR. Determination of such amounts is within the skill of the art.

A particularly useful stain for use in enzyme-linked antibody assays employs peroxidase, hydrogen peroxide and a chromogenic substance such as aminoethyl carbazole. The peroxidase (a well known enzyme available from many sources) can be coupled to the antibody specific for deletion mutant EGFR or merely complexed to it via one or more antibodies. For example, a goat anti-peroxidase antibody and a goat antibody specific for deletion mutant EGFR can be complexed via an anti-goat IgG. Such techniques are well known in the art. Other chromogenic substances and enzymes may also be used.

Radio-labeled antibodies may be specific for deletion mutant EGFR or second antibodies immunoreactive with antibodies specific for deletion mutant EGFR. Again, such techniques are well known. The precise technique by which mutant EGFR is detected in glioma patients is not critical to the invention. Biochemical or immunological techniques can now be used which do not employ immunohistochemistry, although that is a preferred method of the present invention.

One particularly preferred method of detecting and-/or quantitating deletion mutant EGFR protein in solubilized samples employs a competitive assay. An antibody immunoreactive with an epitope found on deletion mutant EGFR but not found on normal EGFR is attached to a solid support such as a polystyrene microtiter dish or nitrocellulose paper, using techniques known in the art. The solid support is then incubated in the presence of the fluid to be analyzed under conditions where antibody-antigen complexes form and are stable. Excess and unbound components of the fluid are removed and the solid support is washed so that antibody-antigen complexes are retained on the solid support. A fixed amount of a polypeptide containing an epitope found on deletion mutant EGFR but not found on normal EGFR, is then incubated with the solid support. The polypeptide binds to an antibody immunoreactive with mutant EGFR which is attached to the solid support. The polypeptide has been conjugated to a detectable moiety, such as biotin, peroxidase or radiolabel, by means well known in the art. Excess and unbound polypeptide is removed and the solid support is washed, as above. The detectable moiety attached to the solid support is quantitated. Since the deletion mutant EGFR and the polypeptide have competed for the same antibody binding sites, the solubilized mutant EGFR in the fluid to be analyzed can be quantitated by its diminution of the binding of the polypeptide to the solid support. Antibodies employed in this assay may be immunoreactive with deletion mutant EGFR but not with normal EGFR. Alternatively, relatively specific antibodies may be used under conditions which destabilize immunoreactivity with normal EGFR. Polyclonal antibodies which contain an antibody species immunoreactive with an epitope on deletion mutant EGFR but not on normal EGFR, may also be used.

A preferred diagnostic method for determination of Type III gliomas involves differential detection of the intracytoplasmic and extracytoplasmic domains. This detection may be on the gene or peptide level. On the gene level, nucleotide probes specific for the intracytoplasmic domain (base numbers 2192-3720 on FIG. 11) and for the extracytoplasmic domain (base numbers 190-2122) are used. DNA extracted from Type III gliomas will hybridize with the intracytoplasmic but not the extracytoplasmic probes. Similarly, detergent solubilized membrane proteins from suspect tissue samples can be tested immunologically using antibodies specific for epitopes found in the intracytoplasmic and the extracytoplasmic domains. The antibodies can be prepared by immunizing mammals with peptides expressed from the sequences corresponding to these domains, as indicated above, and selecting those antibodies specific to each domain using techniques that are well known to those skilled in the art. The membrane protein fraction from Type III gliomas will react with antibodies to the intracytoplasmic domain of EGFR but not with antibodies specific for most the extracytoplasmic domain. The particular procedures for gene probe assays and immunoassays will be well-known to those skilled in the art. Similarly, antibodies specific for Type III EGFR mutant proteins can be used. Such antibodies will react with the epitopes which are not present on intact EGFR.

Treatment may be with radioactive isotopes including $^{131}$I [Bullard et al. (1986) and Lee et al. (1988)] or appropriate drugs also conjugated to those antibodies. A number of treatment protocols employing monoclonal and polyclonal antibodies have been developed in the art of cancer therapy which are useful for the present invention. Each of these protocols depends on the specificity of the antibody as a targeting agent for their respective tumor antigen: 1) immune system effector cells—either endogenous (Sears, 1984 & 1985, colorectal carcinoma; Meeker, 1985, B lymphocyte malignancy; Shouval, 1987, liver cancer) or isolated from the patient and reinjected; (Sears, 1982, and Douillard, 1986, colorectal carcinoma) 2) cytotoxic drugs; (EPO 0153 144, ricin) or 3) radioactive isotopes (Carrasquillo, 1984, directing $^{131}$I to metastatic melanoma). In each case, the role of the antibody is to direct the active agent to particular tumor cells whose surfaces carry antigens corresponding to the respective antibodies.

Treatment comprises administration to a glioma patient of an effective amount of an antibody specific for the mutant EGFR and unreactive with normal EGFR, said antibodies optionally labelled with radioactive elements or conjugated to cytotoxic drugs. See, U.S. Pat. Nos. 4,454,106 and 4,472,509 which are expressly incorporated herein by reference. The appropriate level of antibody for treatment can be determined for each patient using standard methods and no more than routine experimentation.

The following examples are included for illustrative purposes only and are not intended to limit the scope of the invention.

EXAMPLES

In the examples, we determined the effect of rearrangements on the structure of the EGFR gene product in five human glial tumors. The target of each of these alterations was the extracytoplasmic domain. Three types of altered transcripts were identified.

Source of Tumor Material

The xenografts used in the present study were derived from surgical biopsies of malignant human gliomas. Their establishment and karyotypes have been described previously (Humphrey et al., 1988). Southern blotting experiments with EGFR cDNA probes have shown that five of the xenografts (D245MG, D256MG, D270MG, G298MG and D317MG) contain rearranged and amplified EGFR genes. The same rearranged fragments were detected in the original tumor biopsies (Humphrey et al., 1988).

Tumor xenograft D320MG exhibited amplified EGFR genes without any detectable rearrangements. Xenografts D263 and D274 exhibited no amplification or rearrangement of the EGFR gene. Therefore, five of the 8 glioma xenografts examined contained rearranged and amplified EGFR genes which were all present in the initial tumor biopsy.

Cloning of the EGF receptor gene demonstrates Internal Deletions in human glial tumors To analyze the structure of the altered EGF receptor genes, a map of the gene was constructed. We generated a genomic phage library using DNA from D320MG. The human glial tumor xenograft has an approximately ten-fold amplification of the EGFR gene but no detectable rearrangements on Southern blot hybridization. The library was screened with fragments from a 5.5 kb EGF receptor cDNA clone (Ullrich et al., 1984).

Forty-eight phage clones were obtained and used to assemble an EcoRI map of the EGF receptor gene (FIG. 4A). The clones spanned the entire gene except for two small gaps. Southern blot hybridization (using genomic DNA digested with various enzymes) confirmed that the clones identified all EcoRI fragments within the gene (including those containing the gaps). The map deduced using these tumor-derived phage clones was not rearranged in comparison to normal genomic DNA.

Figure 11(1):
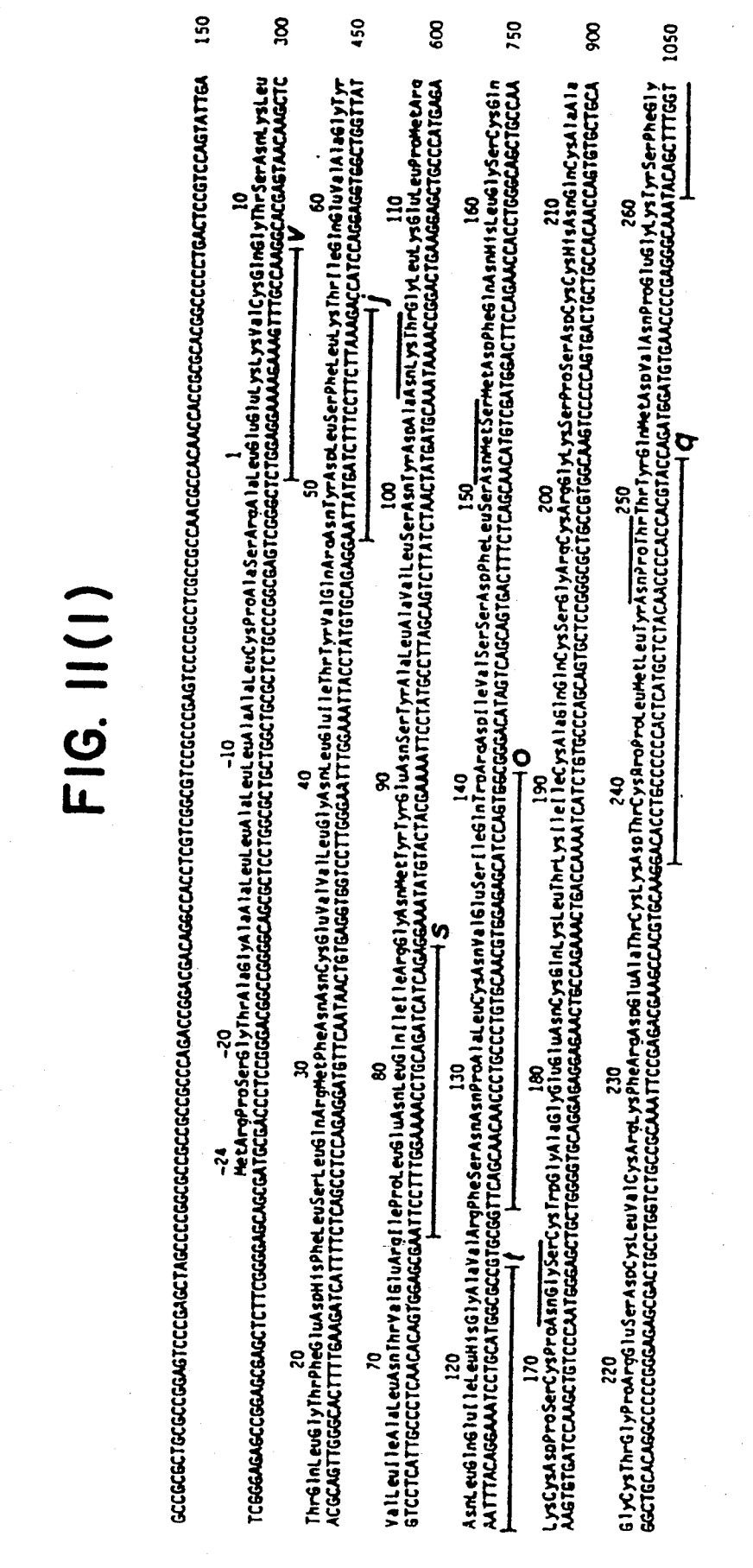
Figure 11(2):
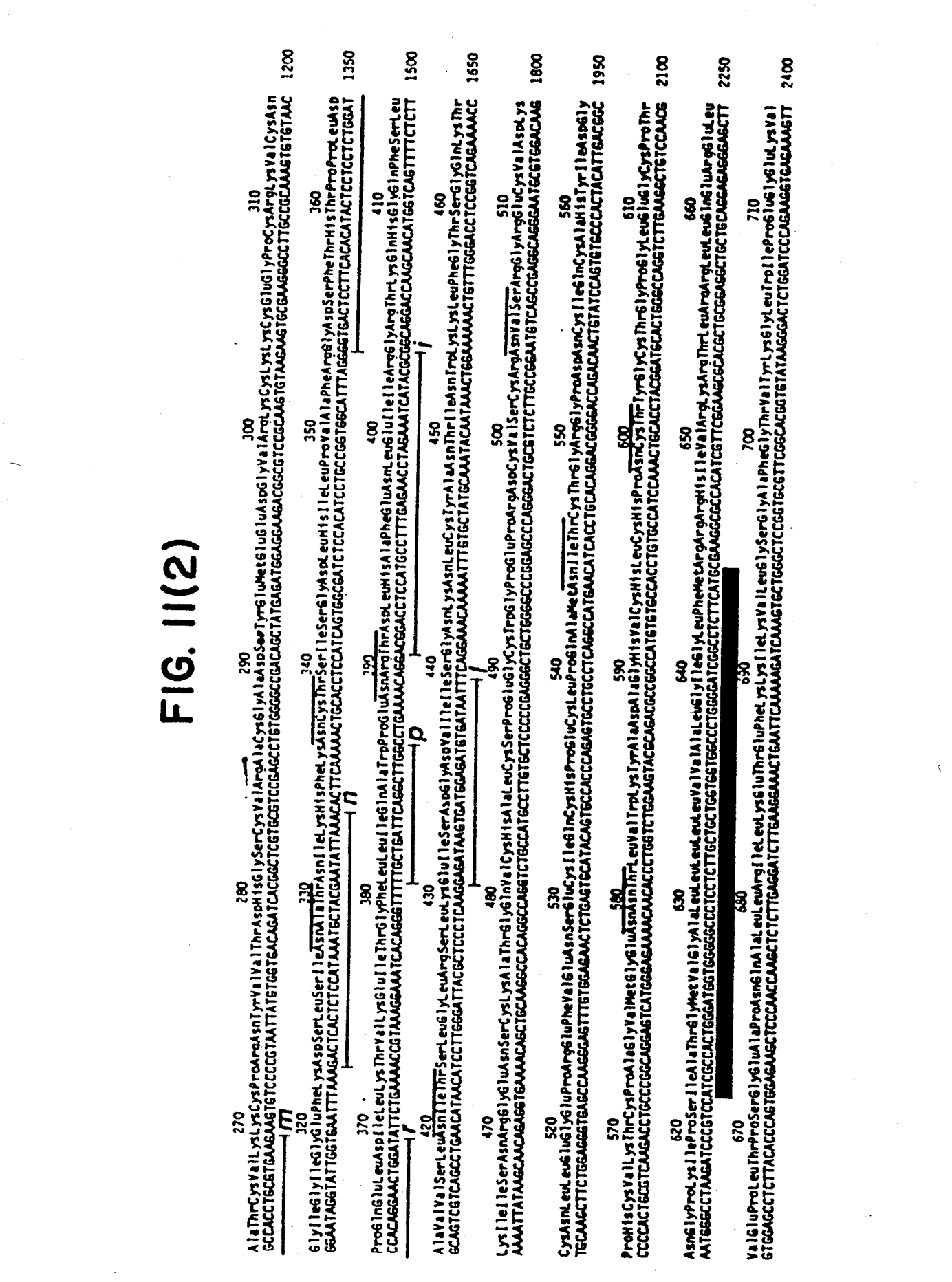

A map of the EGF receptor gene has been published by Haley et al. (Haley et al., 1987b). Our map agrees with Haley et al. except that the size of some of the fragments differ for unknown reasons. In addition, our map includes several small EcoRI fragments not included previously. The extracytoplasmic and transmembrane domains are located at base numbers 186–2121 and base numbers 2122–2191, respectively for EGFR genes (FIG. 11).

Clones corresponding to the extracytoplasmic domain of the gene were used as hybridization probes with Southern blots of EcoRI digested tumor DNA (FIG. 4C). Each genomic clone revealed a deletion and/or a rearrangement in at least one of the five tumors in which we had previously demonstrated rearrangements using EGFR cDNA probes (Humphrey et al., 1988).

Based on the information obtained from Southern blots probed with genomic phage clones, the approximate areas of deletion within the EGFR gene in each tumor were deduced (FIG. 4B). While none of these rearrangements were identical at the genomic level, the deletions in D256MG and D298MG were around a central locus. Tumors whose genomes carry this central deletion are designated Type I. The deletions in D2709MG and D317MG centered around a locus at the 5′ end of the gene. Tumors whose genomes carry this end deletion are designated Type II. The deletion in D245 appeared to involve most of the extracytoplasmic portion of the gene. Tumors whose genomes carry this deletion are designated Type III.

Summary of EGFR Mutant Type Analysis

Phage clones 40 and 24 revealed deletions and rearrangements in Type II tumors D270 (FIG. 4C, lane C) and D317 (data not shown), but not in Type I tumors D256MG or D298MG. Conversely, clones 26 (FIG. 4C) and 29 (data not shown) demonstrated a rearrangement in tumors D256MG (FIG. 4C, Lane B) and D298MG (lane E) but not in tumors D270 or D317. The abnormally migrating fragments were unlikely to be the result of restriction fragmentation length polymorphisms (RFLPs) since new bands were also observed when the tumor DNA was digested with several other enzymes.

Using EcoRI subfragments of phage clone 26, the 2.5 kb fragment in Type I tumor D256 (FIG. 4C, phage clone 26, Lane B) was shown to be due to a rearrangement affecting the 8.0 kb and 1.8 kb fragments (FIG. 4A). The fact that the normal size 8.0 kb fragment was still present at increased copy number in tumor D256 could be due to the presence of the several copies of chromosome 7 which were detected cytogenetically in metaphase spreads from this xenograft (Bigner et al., 1986). Such numerical increases in chromosome 7 are common in glial tumors. As an alternative explanation, some of the amplification units in D256 may be heterogeneous with some units containing the normal 8.0 kb fragment and others containing the rearranged 2.5 kb fragment.

Phage clones ERG-9, 40, and 24, demonstrated no amplification in Type III tumor D245MG (FIG. 4C, lane A). However, the phage ERG 26 probe, which hybridized to seven EcoRI fragments present in normal DNA, revealed only two amplified fragments in this tumor: a normal size 8.0 kb fragment and an abnormally migrating 1.7 kb fragment. These results suggested that the 5′ part of the EGF receptor gene was deleted in D245MG.

Detailed Analysis of Type III Rearrangement

Figure 5A:
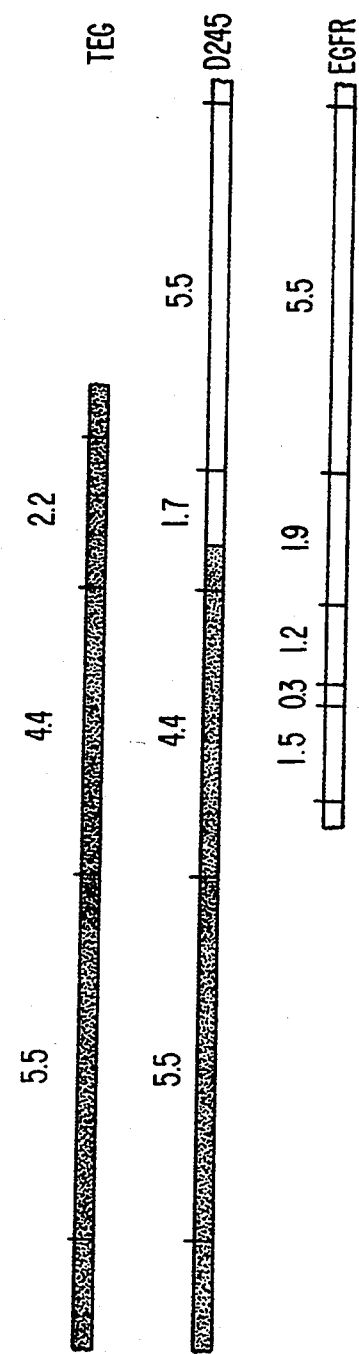

To better understand the nature of this deletion/rearrangement in tumor D245MG, we cloned the 1.7 kb EcoRI fragment containing the presumptive rearrangement from the tumor xenograft (FIG. 4C, Phage clone 26, Lane A), and subsequently used this clone to isolate the sequences giving rise to the rearrangement. The three phage clones spanning the site of recombination are shown in FIG. 5A. The sequence marked "EGFR" is derived from the normal EGF receptor gene (Ullrich et al., 1984), the "D245" sequence is derived from the amplification unit of D245MG, and the "TEG" sequence is derived from the normal locus (referred to as TEG for Truncated EGF Receptor) which had recombined with the EGFR gene to produce the rearrangement in D245MG. Cross hybridization and restriction mapping indicated that the 1.7 kb EcoRI restriction fragment from the D245MG DNA was the product of a rearrangement between a 1.8 EcoRI fragment from the EGFR locus and a 2.2 kb EcoRI fragment from the TEG locus.

The three fragments were subcloned into plasmid vectors and partially sequenced. The nucleotide sequences are presented in FIG. 5B and diagrammed in FIG. 5C. Several features of the sequences were notable: (i) the rearrangement occurred within an intron upstream of the EGF receptor exon corresponding to nucleotides 1818 to 1908 of the EGFR cDNA sequence; (ii) an 18 nucleotide A-T rich motif was repeated four times in the vicinity of the breakpoint in the rearranged fragment, but only once in the corresponding part of the TEG fragment; (iii) at the site of recombination, seven additional nucleotides were present which did not appear to be derived from either the TEG or EGF receptor loci; and (iv) Alu-type repeats were present in both the TEG and EGF receptor derived fragments and one such repeat is present in the clone containing the rearrangement.

Figure 5E:
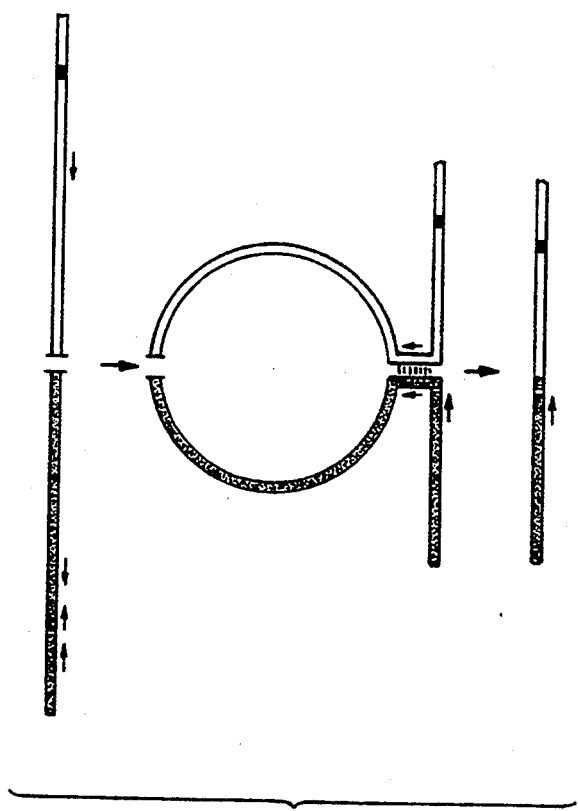
Figure 5C:
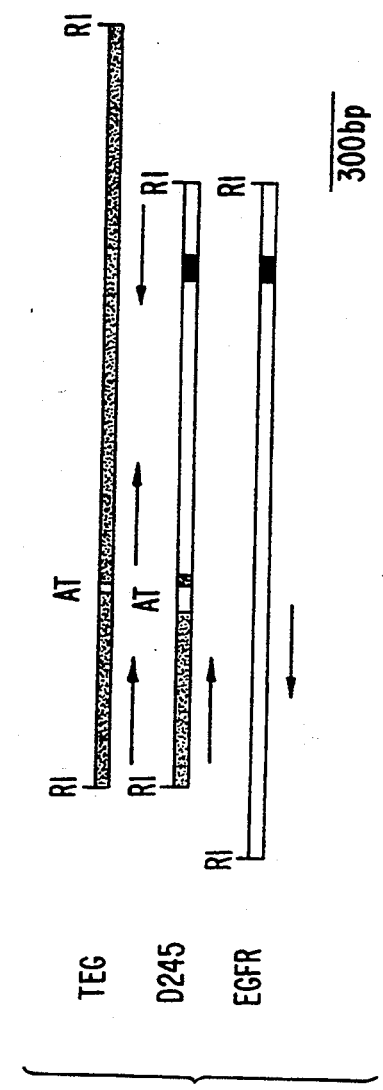
Figure 5D:
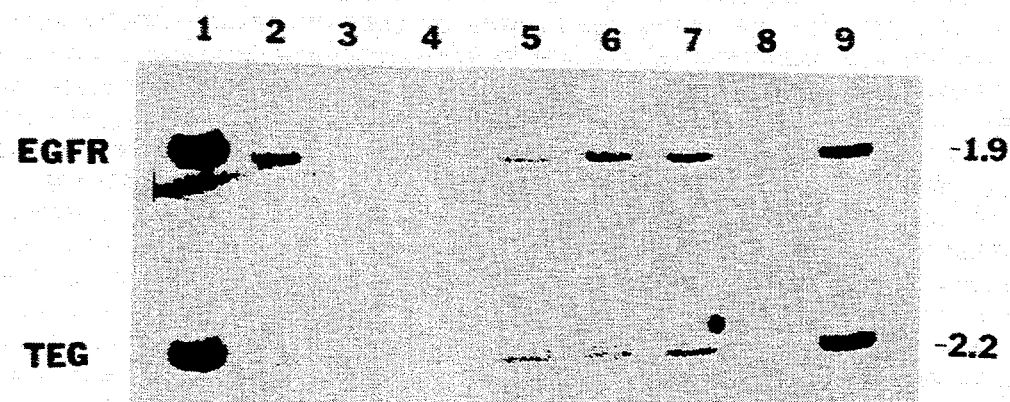

To determine the normal chromosomal position of the TEG locus, we screened human-mouse somatic cell hybrids with the TEG specific probe. This demonstrated that TEG, like the EGF receptor gene, was located on chromosome 7. Further hybridization to hybrids containing various deletions on chromosome 7 (Bartels et al., 1986; Zergerling et al., 1987), showed that both TEG and the EGF receptor were located in the same subchromosomal region at 7p12–7p14 (FIG. 5D). Thus, the rearrangement in D245 was intrachromosomal. The juxtaposition of Alu sequences around the breakpoints (FIG. 5C) suggested a model for the D245 recombination similar to one proposed for the LDL receptor (Lehrman et al., 1985), wherein hairpin stemloop structures composed of Alu-type repeats mediate an intra-strand recombination event (FIG. 5E). The significance of the A-T rich repeat is unclear, but a hotspot of recombination in a mouse model of gene amplification occurred within the context of an A-T rich area and Alu-type repeats (Hyrien et al., 1987).

The protein produced in D245MG is similar to v-erb B

To determine the effect of the truncation on the gene product, we first performed Northern blot analysis using poly A+ selected RNA from the xenograft of D245MG. When probed with sequences derived from the 3' half of the EGF receptor cDNA, normal placenta showed the expected 10.0 and 5.5 kb transcripts, but abnormally migrating bands of 9.0 and 4.8 kb were obtained with RNA from tumor D245. When the blot was hybridized with a probe from the 5' half of the EGF receptor cDNA, the same 10.0 and 5.5 kb bands were detected in placenta, but no transcript was found in RNA from D245MG. This was consistent with the Southern blot and genomic cloning data which had suggested that a deletion of the 5' end of this gene had occurred.

To determine the nature of the aberrant transcript from D245 cells, we constructed a cDNA library using poly A+ selected RNA from the D245 xenograft. A combination of restriction endonuclease mapping and partial sequence analysis of 17 different cDNA clones selected with a probe for the EGF receptor gene showed that they were identical to published sequences of EGF receptor mRNA from nucleotide 885 to the 3' end of the coding region (FIG. 6C). The sequences 5' to nucleotide 885 of the D245 cDNA clone were not homologous to EGF receptor cDNA and were apparently derived from the upstream locus. Search of a DNA database (Gen Bank, release 52.0) revealed no significant homologies of this sequence to any known sequence. Open reading frame (ORF) analysis upstream of nucleotide 885 showed numerous stop codons in three reading frames. The single long open reading frame began at D245 cDNA nucleotide 955 (FIG. 6) and continued in the native reading frame of the EGF receptor. The nucleotides surrounding the first methionine codon (GCCATGA) within this ORF were in good agreement with the canonical initiator sequence (Kozak et al., 1987). Thus, it is likely that the translation product of this RNA had an N-terminus corresponding to amino acid 543 of the EGF receptor protein and that the open reading frame was preceded by a long 5' untranslated sequence. The predicted protein product of this mRNA would be a truncated version of the normal receptor containing 644 amino acids, a predicted molecular weight of 72 kd, and retention of 3 N-linked glycosylation sites (Ullrich et al., 1984). Comparison of the predicted amino acid sequence from the D245 EGF receptor gene with that of v-erb B oncogenes (Fung et al., 1984; Yamamoto et al., 1983; Nilsen et al., 1985; Gammett et al., 1986) revealed that the protein product of the tumor is very similar (and in fact only 8 amino acids longer) to several avian retroviral gene products described previously.

Detailed Analysis of Type I and Type II Transcripts

We first employed RNase protection to analyze the transcripts from the four other tumors with EGFR rearrangements. In addition to being able to detect deletions in mRNA, this technique can reveal a significant fraction of point mutations (Winter et al., 1985). The probes used to analyze total RNA from these tumors are shown in FIG. 7A. Probe I contained a 910 base pair fragment from the 5' end of the cDNA. It yielded a fragment of 910 bp from all RNA samples tested (FIG. 7C); in the RNA samples from the tumors with rearrangements, the normal size fragments were probably a result of transcription from the remaining normal EGFR gene. In previous cytogenetic experiments, we have shown that at least two copies of chromosome 7 remain in each of these four tumors (Bigner et al., 1986). In tumors D270 (FIG. 7C, probe I, lane C) and D317 (Lane F), the most intense fragment detected was approximately 230 bp; these new fragments appeared to be expressed at a considerably higher level than the normal size 910 bp fragment, especially when the difference in size was taken into account.

Probe II revealed 210–215 base pair fragments in tumors D270 and D317 as well as less intense 914 base pair fragment corresponding to the normal transcript (FIG. 4C, probe II, lanes C and F). The cluster of closely migrating fragments (rather than a single band) was most likely due to imperfect cleavage of the duplex; RNase protection experiments in which similar RNA probes were hybridized to cloned genomic fragments also produced a cluster of fragments. The data obtained with probes I and II were consistent with the hypothesis that the deletion in both tumors D270 and D317 resulted in an approximately 800 base pair deletion near the 5' end of the transcript. While the genomic deletions were not identical (FIG. 4), it appeared that the two tumors had lost similar exon sequences.

Probe III demonstrated the normal 970 base pair fragments in D270 and D317 (FIG. 7C, probe III, lanes C and F), but 450 and 250 bp fragments were observed in D256 and D298 (Lane B and E), suggesting an approximately 270 base pair deletion within the transcript of these latter two tumors. Tumor D245 also had an abnormal RNase protection pattern (FIG. 7C, probe III, lane A); the 495 bp fragment in D245 corresponded to the break point in the transcript determined from the cDNA clones. Probes specific for the 3' half of the receptor (including the tyrosine kinase domain and autophosphorylation sites) showed no abnormalities in any of the five tumors, indicating that there were not point mutations detectable by this method.

The Rearrangements Result in In-Frame Deletions

Figure 8A:
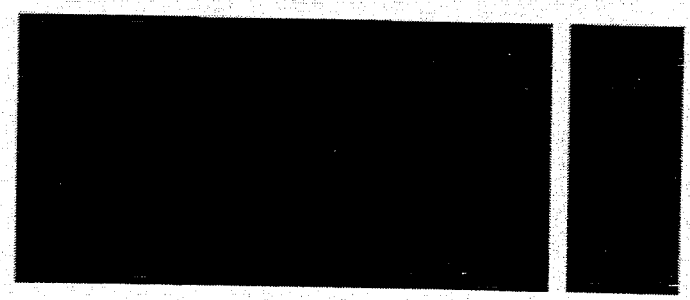

The RNase protection and genomic Southern blot data provided an approximation of the nature of the deletion, but it was difficult to determine the precise nature of the abnormalities. For this purpose, the polymerase chain reaction (PCR) was used to generate cDNA fragments from the mutant alleles. The data from the RNase protection experiments and published information on the normal EGFR cDNA sequence was used to guide the choice of primers. cDNA was generated by first annealing the 3' primer to total tumor RNA, and then extended by using MMLV reverse transcriptase. PCR was then carried out using a method similar to that described by Kawasaki et al. (Kawasaki et al., 1988). When RNA from tumors D270 and D317 was analyzed with one set of primers (FIG. 8A) a major fragment of 230 base pairs were produced (FIG. 8A, lanes A and B), while the normal size 1100 base pair fragment was seen only faintly (not shown), consistent with the size of the deletions inferred by the RNase protection experiments. Another glial tumor xenograft, D397, had a Southern blot pattern very similar to that of D270 when probed with the EGFR cDNA. It was analyzed in this PCR experiment and produced a fragment similar to that from D270 and D317 (FIG. 8A, lane C). A second set of primers revealed a fragment of 220 base pairs in tumors D256 and D298 (FIG. 8A, lanes D and E respectively), instead of the normal size 440 base pairs which was found with D320 RNA (lane F); the 220 bp fragment size was consistent with the data from the RNase protection experiments.

PCR products of the four tumors were subcloned and sequenced. The sequences from tumors D270, D317 and D397 were all identical (FIG. 8B), and the sequence derived from tumor D256 was identical to that from D298 (FIG. 8C). In all cases the deletions did not alter the reading frame and reconstituted a glycine codon at the deletion site.

Discussion

We have demonstrated that rearrangements of the EGFR gene in human glial tumors often result in specific deletions of the extracytoplasmic domain of the molecule. While coding information was lost from this domain, the reading frame of the receptor was precisely preserved in every instance. Our results confirm and extend the observations made by other workers using Southern blot assays on glial tumors. Libermann et al. (Libermann et al., 1985) noted that two glial tumors with DNA amplification had apparent rearrangements that were detected with cDNA probes from the extracytoplasmic domain. Similarly, Yamazami and co-workers (Yamazaki et al., 1988) and Malden et al. (Malden et al., 1988) detected rearrangements in two glial tumors and found that these produce protein products of abnormally small size. Recently, a 190 Kd protein has been isolated from a glial tumor cell line which did not appear to be the result of any gross genetic rearrangement, but peptide mapping suggested that the additional material was due to an addition in the extracytoplasmic domain (Stech et al., 1988).

In a previous publication, we examined the size of the proteins produced in these xenografts and their effect on EGF binding affinity (Humphrey et al., 1988). As would be predicted from the sequence data presented here, the protein isolated from D245 is unable to bind EGF but can be autophosphorylated. The major polypeptide detected with antibodies against the intracytoplasmic domain of the receptor was 77 kilodaltons following deglycosylation, consistent with the 72 kilodaltons predicted from the cDNA sequence. The proteins immunoprecipitated from tumors 270 and 317MG were 150 kilodaltons (predicted polypeptide size of 120,000) and those from D298 and D256 were 130 kilodaltons (predicted polypeptide size of 100,000). The differences in size from that predicted from the cDNA sequences may reflect the degree of glycosylation, as there is a similar difference between the predicted molecular weight of normal EGFR protein and its mobility on SDS gels. The binding affinity for EGF in these tumors was less than three-fold lower than that of the control cell lines with normal EGFR gene sequences. Thus, the deletions do not seem to substantially affect EGF binding, although the normal receptors that are still present in these tumors complicate this conclusion. The domain thought to be responsible for EGF binding (Lax et al., 1988) was not deleted in any of the tumors except for D245MG.

Several facts suggest that the alterations noted here play an important role in glial tumor development. First, in humans, gene amplification only appears in tumor cells (Alitalo et al., 1984), and with the exception of B and T lymphocytes, genetic rearrangements have only been associated with disease. Second, EGFR gene amplification in glial tumors Is a clonal event (i.e., amplified genes appeared to be present in nearly every cell of the tumor (Wong et al., 1987). Third, amino-terminal truncations in v-erb B are known to be crucial for their effect; in all of the tumors studied here, the alterations were confined to the amino-terminal domain. In one tumor, the deletion resulted in a truncation remarkably similar to that found in v-erb B oncogenes.

When EGF binds to the normal receptors, autophosphorylation and activation of the kinase domain occurs within minutes, and receptor down regulation through endocytosis and degradation of the ligand receptor complex are completed within one hour (Carpenter et al., 1987). The products of the v-erb B oncogene are thought to be oncogenic because the truncation results in a protein whose kinase activity is constitutively active and unregulated (Downward et al., 1984). The structural alterations occurring in D245MG may result in a similar activation of the receptor kinase, allowing it to function in the absence of the natural ligand. It has recently been demonstrated that over-expression of a protein lacking the EGF binding domain can transform Rat 1 cells and activate the tyrosine kinase (Haley et al., 1989). The deletions in the other tumors studied occurred within one of the two cysteine rich domains in the receptor. Therefore, these alterations could also result in a conformational change that might leave the receptor in an abnormally active or unregulated state.

Finally, one must ask why the rearrangements occur in amplified genes of some gliomas while other similar tumors contain amplified but otherwise apparently normal genes. One possibility is that a certain subset of glial tumors are dependent on the over-expression of EGF receptors. Evidence in support of this possibility comes from recent in vitro experiments in which transformation of NIH 3T3 cells by over-expression of the EGF receptor required the presence of EGF (Di Fiore et al., 1987; Riedel et al., 1988; Velu et al., 1987) and the demonstration that some glial cell lines contain TGF alpha transcripts (Nister et al., 1988). Extrapolating the in vitro data to the in vivo state, tumors possessing a high density of normal receptors might be activated by otherwise limiting quantities of EGF or TGF-alpha present in the area surround and including the tumor.

A second subset of tumors might have altered receptors whose structure results in a molecule that is constantly active and is only partially or not at all regulated by ligand. Such independence from the normal signals controlling cellular growth is the essence of tumorigenesis. Tumor types I, II, and III appear to be of the second subset.

METHODS

DNA Hybridization

DNA was purified using Proteinase K-SDS and extracted with phenol and chloroform (Vogelstein et al., 1987). DNA (4 ug) was digested with EcoRI (BRL) using buffers and conditions specified by the manufacturer, and after electrophoresis through a 1% agarose gel, transferred to nylon membranes (Bio-Rad) using 0.4N NaOH (Reed et al., 1985). Pre-hybridization and hybridization were done as described previously (Vogelstein et al., 1987). Probes were labelled with d-$^{32}$PdCTP using the oligolabelling method (Feinberg and Vogelstein, 1984). Repeated sequences were removed by the pre-association method of Sealey et al. (Sealey et al., 1985).

Library Construction

The genomic library was constructed from D320MG as described previously (Ruppert et al., 1988). After partial Mbo I digestion, DNA was size-fractionated through sucrose density gradient ultracentrifugation. The fractions containing 17 to 24 kilobase fragments were cloned into the Bam HI site of Lambda Fix (Stratagene) after partial fill-in of Mbo I ends. The ligation product was packaged with lambda phage extracts (Stratagene) and used to infect E. coli C600 cells. DNA from the resulting plaques was lifted with Colony Plaque Screen membranes (Dupont, NEN Research Products) and screened with EGF receptor cDNA probes (Ullrich et al., 1984; Merlino et al., 1985).

To clone the 1.7 kb rearranged fragment, D245 DNA was digested with EcoRI and size selected by electrophoresis on a 1% agarose gel. DNA was eluted from the gel (Vogelstein et al., 1987), ligated to gt10 arms (Promega), packaged with lambda phage extracts and used to infect C600 cells. The library was screened with an EGFR cDNA probe and a clone containing the 1.7 kb rearranged fragment was identified. To clone the TEG locus, a total genomic library was first made from D245MG DNA and screened with the 1.7 kb rearranged EcoRI fragment, resulting in a 15 kb phage clone bridging the rearrangement between TEG and EGF receptor loci. The 4.4 kb fragment from this phage clone was then used to screen a genomic library made from D259 (a glial tumor cell line without EGFR amplification or rearrangement) to clone the normal TEG locus. The fragments from D245, EGFR and TEG participating in the recombination were subcloned into pBluescript (Stratagene). For sequencing, nested deletions were generated using exonuclease III and mung bean nuclease (Henikof et al., 1984). Plasmids were transformed into HB101 cells (F+::Tn5) and single stranded DNA prepared using R408 helper phage (Russel et al., 1986). Sequencing by the di-deoxy method was done using a modified form of T7 polymerase (USB).

Northern Blotting and cDNA Library Construction

For Northern analysis, poly(A)+RNA was isolated from 10 ug total RNA by selection on oligo-dT cellulose, separated by electrophoresis through a 1.5% MOPS/formaldehyde gel and transferred in dilute alkali to nylon (Bio-Rad). For construction of the cDNA library, first strand cDNA was prepared using MMLV reverse transcriptase (BRL) and random hexamer primers (Pharmacia). The second strand was synthesized using the method of Gubler and Hoffman (Gubler et al., 1983). The resulting cDNA was methylated with EcoRI methylase and ligated to EcoRI linkers (New England Biolabs). The linked cDNA was cleaved with EcoRI, and fragments > 1.0 kb were isolated following electrophoresis through a 1% agarose gel. This cDNA was ligated into ZAP (Stratagene) and packaged with phage extracts (Stratagene). The library was screened with an 0.7 kb TaqI-EcoRI fragment derived from the EGFR end of the 1.7 kb EcoRI fragment of D245 (See FIG. 5A). Plasmids containing inserts were derived from phage plaques by using the excision process recommended by the manufacturer.

Ribonuclease Protection

Total RNA was isolated by the acid-guanidium extraction method described by Chomeynski and Sacchi (Chromezynski et al., 1987). 32P-labeled RNA transcripts were generated in vitro from subclones of EGFR cDNA using T3 or T7 RNA polymerase. The probes used were: Probe I: a 910 bp SmaI-ClaI fragment of pE15 (Merlino et al., 1985); Probe II: a 730 bp EcoRI-Bam HI fragment from pE7 (Xu et al., 1984); Probe III: a 970 bp Bam HI-EcoRI fragment from pE7. Ribonuclease protection was performed as described (Winter et al., 1985) with the following modifications: hybridizations were performed in a final volume of 10 ul; only RNase A at 12.5 ug per ml was used; and the RNase A and Proteinase K digestions were performed at room temperature for 30 minutes.

PCR amplification of cDNA products

To generate first strand cDNA, 50 pmol of the 3' primer was annealed to 1 ug of total RNA by cooling from 60° C. to 37° C. over ½ hour in the presence of 400 uM of each deoxynucleotide, reverse transcriptase buffer (BRL), 1 U of placental RNase inhibitor (Promega) in a total volume of 25 ul. This was followed by the addition of 20 U of MMLV reverse transcriptase (BRL) and incubation at 37° C. for 10 min. PCR was carried out on this sample by diluting the sample to 50 ul, adjusting the final MgCl$_2$ concentration to 2.5 mM, and adding 50 pmol of the 5' primer and 2.5 U of Taq polymerase (Cetus). Thermal cycling was done at 93° C. for 1 min., 40° for 2 min., and 72° for 2 min. for 35 cycles. The sample was then subjected to electrophoresis in a 2% agarose gel. Following staining with ethidium bromide, the band was excised, the DNA eluted as described previously (Vogelstein et al., 1987) and subcloned into pBluescript (Stratagene) for sequencing. At least two clones for each PCR product were sequenced and some samples were sequenced directly by the method of Winship (Winship et al., 1989). For tumors D270, D317, and D397, primer set A was used, consisting of 5'-AGTCGGGCTCTGGAGGA-3' and 5'-CACTGATGGAGGTGCAGT-3'. For tumors D256 and D298, primer set B was used consisting of 5'-(CTG)CAGGTCTGCCATGCCTTG-3' and 5'-(GGT)ACCATCCCAGTGGCGATG-3'. The sequences in parentheses were not present in the EGFR sequence and were added to complete either a Pst I or Kpn I restriction site.

FIG. 4—Deletions in the EGF receptor gene in human gliomas.

FIG. 4A is an EcoRI map of the Human EGF receptor gene. The sizes of the fragments are indicated in kilobases. Representative phage clones used to assemble the map are shown below it.

FIG. 4B is the deduced EGFR gene structure of five glioma xenografts. The numbers to the left correspond to the glial tumors described in the text. The solid lines indicate sequences present in the tumors, while the approximate points of deletion are indicated by X'S.

FIG. 4C represents a Southern blot hybridization with phage clones demonstrating deletions in the EGF receptor gene. The blots were hybridized with radiolabelled phage inserts, and the numbers above each blot refer to the phage clone used as the hybridization probe. Rearranged fragments are indicated with an asterisk (*). The tick marks to the right of each autoradiograph refer to the sizes of marker fragments in kilobases which are given on the extreme right.

The lanes contained DNA according to the following key:

N: DNA from normal cells
A) D245
B) D256
C) D270
D) D320
E) D298
F) D370

FIG. 5—Characterization of the rearranged fragment from D245.

FIG. 5A is an EcoRI restriction map of genomic clones containing the 1.7 kb rearranged fragment from D245MG and the corresponding unrearranged fragments from the EGF receptor gene and TEG locus. The open box indicates sequences derived from the EGF receptor gene and the shaded box represents the TEG locus. The numbers refer to the sizes of the EcoRI fragments in kilobases.

FIG. 5B shows a partial nucleotide sequence of the area flanking the site of recombination. Other features based on this sequence are shown in FIG. 5C. An 18 nucleotide A-T rich motif is repeated four times (rpt1-rpt4) in the rearranged D245 fragment but only once in the TEG fragment; an insertion has been made to optimize alignment. Seven nucleotides are present at the site of recombination ("Break point") which cannot be aligned with either of the recombination partners. Portions of the Alu repeats present in the TEG and EGF receptor gene are underlined; the arrowhead indicates the orientation of these repeats according to Deininger et al. (Deininger et al., 1981). Numbers to the right are relative nucleotide positions with respect to the D245 sequence.

FIG. 5C schematically shows the presence of Alu repeats (arrows), the A-T rich motif (open box labeled AT) and exon from the EGF receptor (filled box corresponding to EGFR nt 1818-1908) in the 1.77 kb EcoRI rearranged fragment from D245 and the corresponding unrearranged fragment from the EGF receptor gene and TEG locus.

FIG. 5D illustrates chromosomal localization of the TEG locus. A human-mouse somatic cell hybrid panel containing various deletions of human chromosome 7 (20-21) was digested with EcoRI and blotted to a nylon membrane. It was first hybridized with the 2.2 kb EcoRI fragment from the TEG locus (top) and then hybridized with a 1.9 kb EcoRI genomic fragment from the EGFR locus (bottom).

The somatic cell hybrid clones used (and the regions deleted within the hybrids) were:
Lane 1: 5387-3 cl 10 (intact chromosome 7);
Lane 2: It A9 2-21-14 (7p14-pter);
Lane 3: RuRag 6-19 (7 cen-pter);
Lane 4: 2068 Rag 22-2 (7 q22-pter);
Lane 5: 1059 Rag 5 (7 q22-q32);
Lane 6: 7851 Rag 10-1 (7q22-q32):
Lane 7: 194 Rag 6-13-3(7 q32-qter);
Lane 8: Rag (mouse DNA only);
Lane 9: 4 ug of normal human DNA.

FIG. 5E describes a possible mechanism for intrastrand recombination in D245 involving oppositely paired Alu repeats based on the model proposed by Lehrman et al. (Lehrman et al., 1985). Features of the TEG and EGF receptor fragments from FIG. 5C are reproduced here. The oppositely oriented Alu repeats in the EGF receptor gene and TEG locus on chromosome 7p could base pair forming a stem loop structure. Recombination at the stem would result in the rearrangement seen in D245.

FIG. 6—Characterization of the transcript in D245.

FIG. 6 shows a cDNA sequence of the EGF receptor related mRNA from D245. The designation "D245" refers to the nucleotide sequence of a clone derived from tumor D245 and mRNA. The abbreviation "EGFR" refers to the normal EGF receptor cDNA sequences. The term "D245AA" is the deduced amino acid sequence from "D245", which is aligned with that of "v-erb B" (the v-erb B oncoprotein is a fusion protein between viral and EGFR sequences; only the EGFR related sequences are shown). The presumed initiator condon for tumor D245 is underlined. The numbers to the right refer to the D245 sequence.

FIG. 7—Characterization of transcripts by RNase protection.

FIG. 7A is a schematic drawing of the probes used. The 5.5 kb EGF receptor cDNA is diagrammed above. The striped box is the signal peptide, followed by the extracytoplasic domain which is divided into four domains (1-4), with the cysteine rich regions as indicated. The solid box is the transmembrane domain followed by the intracytoplasmic domain containing the kinase domain. The thin lines are the untranslated regions.

FIG. 7B presents the deduced transcript structures from the RNase protection experiments. Symbols are as in FIG. 4B.

FIG. 7C depicts RNase protection experiments using RNA from the glial tumor xenografts. The numerals I–III refer to the probes in FIG. 7A. The numbers to the right refer to the sizes of the protected fragments (see text).

The lanes contain RNA from: A) D245; B) D256; C) 2709; D) D320; E) D298; F) D317; G) tRNA (negative control); and H) undigested probe.

FIG. 8—PCR analysis of the gene products from the altered region.

FIG. 8A shows gel electrophoresis of polymerase chain reaction products. The gel shows 1/10th of the reaction after 35 cycles.

The lanes contained products from: A) 270; B) 317; C) 397; D) 256; E) 298; F) 320. Primer set A was used for D270, D317, and D397; primer set B was used for D256, D298, and D320 (see Experimental Procedures). The numbers refer to the sizes of fragments in base pairs judged from co-electrophoresed markers.

FIG. 8B shows a sequence of the PCR products from tumors D270, D317, and D397.

FIG. 8C illustrates the sequence of the PCR products from D256 and D298. The numbers and asterisks refer to the EGF receptor cDNA nucleotides flanking the deleted area. The sequence to the right and left of those shown in the figure were the same as in normal EGFR cDNA.

Antibody Production

1. Mice

Mice for the production of hybridomas (later to be fused into a myeloma) were injected according to the schedule below. Mice populations were at least 5 and generally up to 10 in each immunization arm with both Type I and Type II EGFR deletion mutants.

|  | Day | Immunization |
|---|---|---|
| Arm I: | 0 | 100 ug pep–200 ug KLH + CFA id |
|  | 15 | 30 ug pep–60 ug KLH + IFA ip |
|  | 30 | 10 ug pep–20 ug KLH + IFA ip |
|  | 44 | 2.5 ug pep iv |
|  | 105 | 1 ug iv |
|  | 138 | 1 ug iv |
|  | 166 | 1 ug iv |
|  | prefusion titer: greater than 1/2000–1/4000 | |
|  | 181 | 1 ug iv |
|  | 186 | 1 ug iv |
|  | 187 | 1 ug iv |
|  | 191 | fusion |
| Arm II: | 0 | 50 ug pep–100 ug KLH + CFA id |
|  | 14 | 15 ug pep–30 ug KLH ip |
|  | 28 | 1 ug pep iv |
|  | titers: alpha peptide Type I: gtr. than 1/8,000 | |
|  | alpha peptide Type II: gtr. than 1/8,000 | |
|  | 62 | 1 ug pep iv |
|  | 69 | 1 ug pep iv |
|  | 70 | 1 ug pep iv |
|  | 72 | fusion; prefusion serum samples available |
| Arm III: | 0 | 50 ug pep–100 ug KLH + CFA id |
|  | 21 | 1 ug pep iv |
|  | prefusion titer: | |
|  | alpha peptide Type I: gtr. than 1/2,000–1/5,000 | |
|  | alpha peptide Type II: gtr. than 1/4,000–1/19,000 | |
|  | 40 | 1 ug pep iv |
|  | 47 | 1 ug pep iv |
|  | 48 | 1 ug pep iv |
|  | 50 | fusion |
| Arm IV: | 1 | 500 ug pep - 2 - KLH + CFA id |
|  | 18 | 100 ug pep - 2 - KLH + IFA id |
|  | 32 | 50 ug pep - 2 - KLH + PBS ip |
|  | 39 | bled and titered |
|  | 46 | 50 ug pep - 2 - KLH in PBS ip |
|  | 49 | fusion |
| Arm V: | 1 | 500 ug pep - 2 - KLH + CFA id |
|  | 18 | 100 ug pep - 2 - KLH + IFA id |
|  | 32 | 50 ug pep - 2 - KLH + PBS ip |
|  | 39 | bled and titered |
|  | 50 | 2.5 ug free pep - 2 iv |
|  | 54 | fusion |

Abbreviations:
KLH = keyhole limpit hemocyanin
CFA = complete Freund's adjuvant
IFA = incomplete Freund's adjuvant
id = intradermal
ip = intraperitoneal
pep = peptide type I or type II
PBS = phosphate buffered saline Hybridoma supernatants were screened using solid phase radioimmunassy using 0.5 ug/well of pep-2. Hyperimmune sera, specific for pep-2 versus pep-1 preimmune sera was used as baseline controls.

Over twenty-five murine hybridomas making monoclonal antibodies to the EGF receptor mutant peptide (class II) have been isolated.

2. Rabbits

Immunization Schedules

Rabbits were injected with synthetic peptides of the deletion mutant coupled to keyhole limpet hemocyanin initially, and after two months, three further injections at one month intervals. The immunization pattern was performed with rabbits according to the following schedule:

Day −7 Pre-immune bleed (50 ml per rabbit via ear vein)

Day 0 250 ug peptide-KLH conjugate of 1 ml in phosphate-buffered saline; complete Freund's adjuvant (1:1) per rabbit injected subcutaneously with 200 lambda at 5 different sites Day 30 50 ug peptide-KLH conjugate in 1 ml of phosphate-buffered saline; incomplete Freund's adjuvant (1:1) per rabbit injected subcutaneously with 200 lambda at 5 different sites Day 39 Rabbits bled, serum harvested, and stored in 1 ml aliquots at −135° C.

In another experiment, a slightly different schedule was followed.

Three New Zealand white rabbits were immunized with peptide conjugated to KLH. On Day 0, subcutaneous Immunization was administered with 250 μg peptide conjugated to KLH in 1 ml of a 1:1 emulsification of phosphate-buffered saline (PBS) and complete Freund's adjuvant. Each rabbit was injected with this dose at 4 separate sites. On Day 33, each rabbit was boosted at 4 separate sites with 50 μg peptide conjugated to KLH in 1 ml of a 1:1 emulsification of PBS and incomplete Freund's adjuvant. Antisera were obtained by bleeds on Days 40 and 43.

Titration of Antibodies

Antibody titers against peptide were determined in ELISA. Briefly, a concentrated solution of peptide (1 mg/1 ml in PBS) was diluted to 10 μg/ml in 200 mM NaHCO$_3$ buffer (ph 9.2), and 50 μl were added to 96-plate wells of polyvinyl chloride (Dynatech Laboratories, Inc., Chantilly, Va.). The peptide solution was incubated in the plate wells overnight at 4° C. The peptide solution was discarded, and the plates were washed 3 times with Hanks' buffered salt solution containing 0.05% Tween 20 (Sigma, St. Louis, Mo.). Nonspecific binding was then blocked for 1 hr at room temperature with 200 μl of 0.5% bovine serum albumin In PBS. The plates were washed as above. Pre-immune rabbit sera or antisera (100 μl of dilutions in Hanks' buffered salt solution with 0.5% BSA) were added for 2 hr at room temperature. The plates were washed and 50 μl of peroxidase-conjugated goat antirabbit IgG (Zymed Laboratories, Inc., San Francisco, Calif.) was added for 1 hr at 37° C. The plates were washed and 100 μl of substrate solution was added. The substrate solution was prepared by adding 15 mg of o-phenylenediamine (Sigma) to 1 ml methanol, with subsequent addition of 49 ml of deionized water and 50 μl of hydrogen peroxide. Incubation was at room temperature for 15-20 min., and the well absorbances were then measured in an automated plate reader (Titertek Multiskan MCC/340, Flow Laboratories, McLean, Va.) at 492 nm. The ELISA could also be performed with purified antipeptide antibody. The half-maximal titer in this assay was 0.5 μg antipeptide IgG/ml of PBS.

All three rabbits immunized with peptide-KLH conjugate exhibited a marked IgG response as assessed by ELISA against uncoupled peptide bound to plates (FIG. 9). The half-maximal titers (the antiserum dilution at one-half maximal absorbance) varied from 1:6000 to 1:50,000. The binding reaction was specific, as the pre-immune serum from each rabbit was nonreactive; a nonreactive baseline was also obtained when the antisera were reacted with a second 14-amino-acid peptide of different sequence (Pep-1; sequence: H-Asn-Leu-Leu-Glu-Gly-Cys-Thr-Gly-Pro-Gly-Leu-Glu-Gly-Cys-OH).

Purification and Characterization of Antipeptide Antibody

The antipeptide antibody was purified from antiserum by a peptide-Sepharose affinity column with elution by acidic pH. The affinity column was prepared by coupling 5 mg of peptide to cyanogen bromide-activated Sepharose (Sigma), as described in the Pharmacia (Piscataway, N.J.) protocol. The extent of coupling was 100%, as determined by BCA protein assay (Pierce, Rockford, Ill.) of the solution overlying the gel. Ten millititers of antiserum from rabbit 396 (the rabbit with the highest half-maximal titer of 1:50,000 in ELISA in reaction against peptide) were passed over the column, and the column was washed extensively with 500 ml of PBS. Elution was with 100 mM glycine buffer (pH 2.5) with immediate neutralization into 0.4 M Hepes buffer (pH 7.4). A yield of 6 mg of pure IgG was obtained from a starting load of 10 ml of rabbit antiserum 396 (the antiserum with the 1:50,000 half-maximal titer). Lower yields were obtained with purification of antipeptide IgG from antisera of lower half-maximal titers. Elution of active antibody could also be accomplished with 3.5 M $MgCl_2$ (pH 3.5 or pH 6.5). The activity of the antibody eluted under the different conditions was similar, as assessed by ELISA against free peptide.

Control IgG was purified from rabbit pre-immune sera by protein A-Sepharose affinity chromatography. The size and homogeneity of the purified antibodies were monitored under nondenaturing conditions by size exclusion HPLC and under denaturing condition by SDS-PAGE. HPLC was performed on a calibrated 1×30 cm Waters 300 SW column (previously calibrated with standards in the size range of $M_r$ of 20,000-400,000 daltons). Protein elution was followed at 215 nm. SDS-PAGE utilized a 10% resolving gel in the SDS-discontinuous buffer system of Laemmli (Laemmli, Nature (1970), 270:680-688). The protein bands were visualized with Coomassie blue staining. The eluted antibody was identified as IgG by apparent molecular weights on a size exclusion HPLC column and SDS gel (data not shown). Purity was greater than 98%.

Immunocytochemical Detection of Mutant EGFR Expression

The affinity-purified antibody was characterized in immunocytochemistry using frozen tissue sections and the avidin-biotin complex method, as described (Humphrey, et al., Cancer Res. (1988), 48:2231-2238). The tissues tested included a range of normal fetal and adult tissues, carcinomas (prostatic, bladder, breast, and lung), glioma biopsies (-Bx), and gliomas grown in xenograft form in nude mice (-X). The normal tissues, carcinomas, and glioma biopsies were from the Duke University Medical Center Tissue Bank. The glioma xenografts were grown as described (Humphrey, et al., Cancer Res. (1988), 48:2231-2238). The affinity purified antipeptide antibody and the purified pre-immune rabbit control IgG were used at a concentration of 1-2 μg/ml, as determined by initial titration experiments. The antibody could be used in antiserum form with an optimal titer in immunocytochemistry of 1:3000. F(ab')$_2$ fragments of normal rabbit IgG and the antipeptide antibody were also tested in immunocytochemistry on glioma D-270 MG-X and skin. F(ab')$_2$ fragments were generated and purified as described (Colapinto, et al., Cancer Res. (1988), 48:5701-5707). Also used in immunocytochemistry of the glioma biopsies was rabbit antipeptide antibody reactive with the intact EGFR (Product No: OA-11-852, Cambridge Research Biochemicals, Valley Stream, N.Y.). This antiserum was used at a dilution of 1:1000, as established by initial titration experiments.

The antipeptide IgG reacted with the native mutant EGFR in frozen tissue sections fixed briefly with acetone. The antibody specifically recognized only the mutant glioma EGFR and not the intact A431-X squamous cell carcinoma EGFR in both xenograft (data not shown) and biopsy tissue (Table 1). This immunostaining of the mutant EGFR was specific, as purified pre-immune IgG was nonreactive, and preincubation of antipeptide IgG with excess peptide blocked with immunocytochemical staining. In both glioma biopsy and xenograft tissues which bound the antipeptide antibody, the immunostaining was localized to the cytoplasm and cell surface; virtually every tumor cell exhibited immunoreactivity.

Screening of normal and neoplastic tissues by immunocytochemistry with the antipeptide antibody revealed positivity only in a subset of glioblastomas (Table 1). Immunoreactive mutant EGFR was identified in two human glioma biopsies (D-270 MG-Bx and D-317 MG-Bx) and the corresponding xenografts (D-270 MG-X and D-317 MG-X) known to amplify the mutant EGFR gene and express mutant EGFR protein. Four additional glioblastoma biopsies exhibited immunostaining with the antipeptide antibody; one of these (D-397 MG-Bx) was subsequently tested using an RNA-based PCR assay and shown by sequencing to possess the same deletion mutation as gliomas D-270 MG-Bx and D-317 MG-Bx.

Further evidence for the selectivity of this antibody was obtained in this screen of glioma biopsies, as 27 of 27 biopsies reacted specifically with rabbit antipeptide antibody against the intact EGFR; but only those gliomas with the proven (3 cases) or suspected (3 cases)

deletion mutation reacted with the antifusion junction peptide antibody. A range of fetal and adult normal tissues and carcinomas failed to react with the antipeptide antibody, as assessed by this method.

TABLE 1

Antipeptide antibody immunostaining of normal and Tumor tissue frozen sections

| Normal human tissues | Reactivity* | Human neoplastic tissues (biopsies) | Reactivity |
|---|---|---|---|
| Adult | | | |
| Brain | 0/2 | Glioblastoma | 6/35 |
| Muscle | 0/1 | Lung Carcinoma | 0/2 |
| Skin | 0/3+ | Prostatic Carcinoma | 0/2 |
| Kidney | 0/3 | Breast Carcinoma | 0/2 |
| Spleen | 0/2 | Bladder Carcinoma | 0/2 |
| Placenta | 0/11 | | |
| Fetal | | | |
| Brain | 0/1 | | |
| Kidney | 0/1 | | |
| Liver | 0/1 | | |

*Results are expressed as number of positive cases/total number of cases examined.
+Weak Fc receptor binding was observed in one case in epidermal epithelium. This immunostaining was abolished with the use of F(ab')$_2$ fragments.
Note:
Lack of reactivity with normal adult brain and skin was confirmed by immunoprecipitation.

Binding of $^{125}$I-Labeled Antipeptide IgG to Tumor Membranes Expressing Intact and Mutant EGFR The purified antipeptide antibody and pre-immune IgG were both labeled with $^{125}$I at a specific activity of about 1.6 μCi/μg using a variation off the iodogen method as described previously (Colapinto, et al., Cancer Res. (1988), 48:5701–5707). Radioiodinated proteins (22 ng, 50–70 k cpm) were incubated for 2 hr at 4° C. in triplicate with 200 μl of 20 mM Hepes (pH 7.4) containing 0.1% BSA and 40 μl of a 1-mg/ml suspension of microsomal membranes. The membranes tested were from D-270 MG-X, a glioma tumor expressing the in-frame deletion-mutant EGFR; A431-X, a squamous cell carcinoma overexpressing the intact EGFR; and D-245 MG-X, a tumor containing or expressing an EGFR molecule which lacks most of the extracellular domain and serves as a negative tissue control. Following the incubation period, the membranes were separated from unbound activity using 0.22-μm cellulose acetate centrifuge filter units (Spin-x, Costar, Cambridge, Mass.) washed twice with 1 ml of the incubation buffer. The filters had been pretreated by a 30-min incubation at room temperature followed by 3 washes with buffer. Using this procedure, nonspecific binding of radioactivity to the filters was <0.2%. Filters and washes were assayed for $^{125}$I activity in similar counting geometries using an automated gamma counter.

Direct binding of radioiodinated antipeptide IgG to membranes expressing the D-270 MG-X mutant EGFR was significantly higher than to membranes expressing intact EGFR (in A431-X) or a v-erb B-like EGFR (in D-245 MG-X) (Table 2). The specificity of the antipeptide binding reaction was demonstrated by assessing nonspecific binding using $^{125}$I-labeled purified pre-immune IgG. The selectivity of the antipeptide antibody is highlighted by comparing the percentage specific binding values; the level of antipeptide antibody binding to the mutant EGFR in the D-270 MG-X membranes is markedly higher than the low reactivity with intact EGFR, which is similar to that of the negative tumor membrane control.

TABLE 2

Antipeptide antibody binding to membranes of tumors Expressing the deletion mutant EGFR, intact EGFR and v-erb B-like EGFR

| IgG | Tumor | EGFR Structure | Percent Binding | Percent specific Binding |
|---|---|---|---|---|
| Antipeptide | 270 | In-frame deletion mutant | 30.2 | 28.2 |
| Pre-immune | 270 | In-frame deletion mutant | 2.0 | |
| Antipeptide | A431 | Intact | 8.5 | 4.9 |
| Pre-immune | A431 | Intact | 3.6 | |
| Antipeptide | 245 | v-erbB-like | 6.8 | 3.8 |
| Pre-immune | 245 | v-erbB-like | 3.0 | |

Percent binding represents mean fraction of input counts (of a triplicate assay) associated with the membranes. Percent specific binding represents binding of $^{125}$I-labeled antipeptide IgG minus nonspecific binding determined from association of preimmune IgG with membranes. Glioma D-270 MG-X membranes express the in-frame deletion-mutant EGFR and squamous cell carcinoma A431-X membranes overexpress the intact EGFR; glioma D-245 MG-X membranes express a v-erbB-like EGFR which lac ks most of the extracellular domain and serves as a negative tissue control (Humphrey, et al., Cancer Res. (1988), 48:2231–2238; Wong, et al., J. Cell Biochem., Suppl. 13B, Abst. 149).

Reaction of Antipeptide,IgG with Mutant EGFR but not Intact EGFR

The molecular specificity of the antipeptide IgG was tested by immunoprecipitation reaction. The binding in this reaction was followed by EGFR autophosphorylation, SDS-PAGE, and autoradiography, essentially as described. Monoclonal antibody 528 (Ab-1, Oncogene Science, Inc., Manhasset, N.Y.) was used as a positive control, as it will immunoprecipitate both intact and mutant EGFR. Briefly, Triton X-100 detergent solubilized intact A431-X EGFR and mutant D-256 MG-X and D-270 MG-X EGFRs were immunoprecipitated with monoclonal antibody 528 or purified antipeptide antibody. Autophosphorylation with $^{32}$P-ATP was followed by SDS-PAGE with a 7.5% resolving gel. The gel was fixed and dried under vacuum and exposed to X-ray film at −70° C. The antipeptide antibody was used at 20 μg purified IgG or at 100 μl antiserum in binding to Protein A-Sepharose for the immunoprecipitation reaction.

Figure 10:
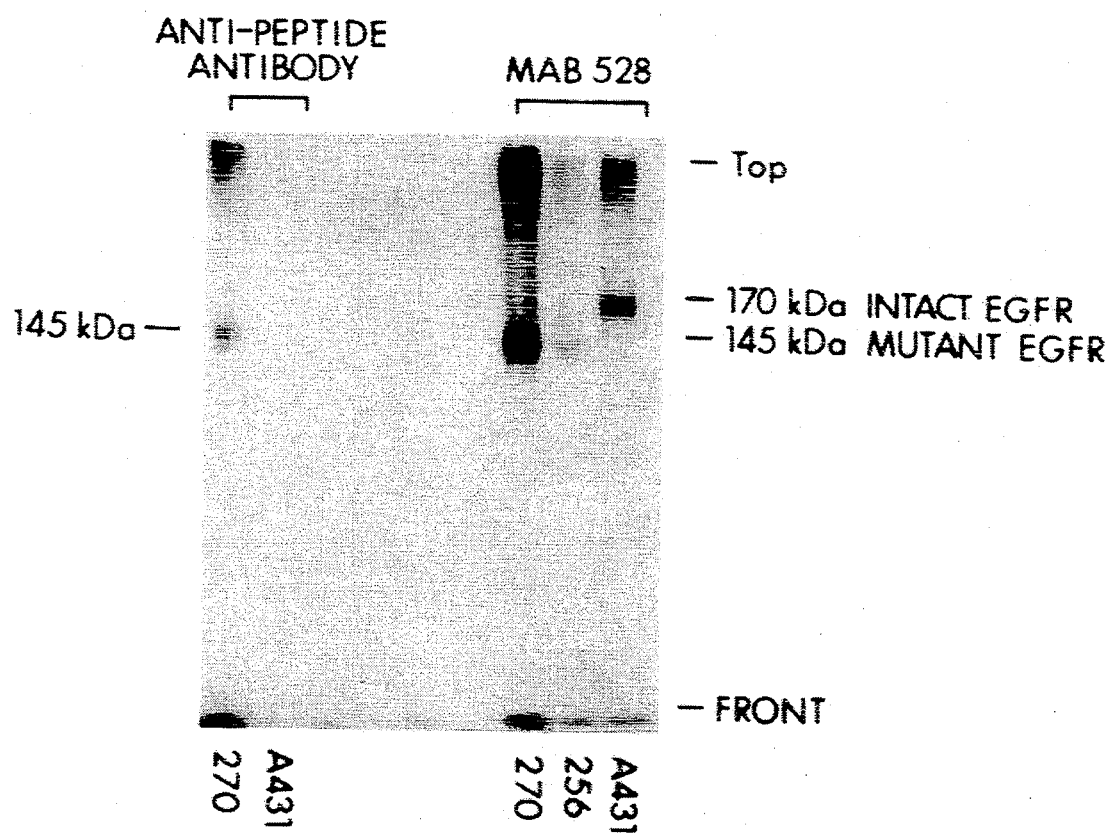

The antipeptide antibody reacted with mutant EGFR in a detergent-solubilized state, as judged by immunoprecipitation, with autophosphorylation and SDS-PAGE (FIG. 10). The positive control immunoprecipitation was with monoclonal antibody 528, which is directed against the EGFR external domain. This antibody reacted with both the intact A431-X and mutant D-270 MG-X EGFR. The antipeptide antibody, in contrast, specifically immunoprecipitated the 145-kDa mutant EGFR in glioma D-270 MG-X and failed to immunoprecipitate the intact A431-X EGFR. Purified preimmune IgG did not immunoprecipitate the mutant EGFR.

Effect of Antipeptide IgG on $^{125}$I-Labeled EGF Binding To the Mutant EGFR and on Mutant EGFR Kinase Activity The effect of the purified antibody on $^{125}$I-labeled epidermal growth factor (EGF) (New England Nuclear, Doraville, Ga.) binding was determined using the reaction mixture of microsomal membranes and $^{125}$I-labeled EGF, as described (Humphrey, et al., Cancer Res. (1988), 48:2231–2238). To determine the effect of antibody on EGFR kinase, the phosphorylation of EGFR in D-270 MG-X and A431-X membranes was performed as described by Davis and Czech (Davis, et al., J. Biol. Chem. (1985), 260:2543–2551). Briefly, the phosphorylation was carried out in a volume of 50 μl consisting of membranes (5–10 μug), 20-mM Hepes (pH 7.4), 4 mM MnCl₂, 10 mM MgCl₂, 1% DMSO, ±400 ng of EGF, ±normal rabbit IgG, ±antipeptide antibody. The mixture was incubated for 20 min at room temperature and then cooled to 4° C. [γ-³²p]-ATP (1.5 μM; 10–15,000 cpm/pmol) was added and the reaction was stopped after 3 min by adding 25 μl of sample buffer containing sodium dodecyl sulfate and betamercaptoethanol. The samples were subjected to electrophoresis on 7.5% polyacrylamide gels (Laemmli, Nature (1970), 270:680–688), and the extent of receptor phosphorylation was visualized by autoradiography.

The anti-synthetic peptide antibody did not affect binding of ¹²⁵I-labeled EGF to the mutant EGFR, nor did it affect either basal or EGF-stimulated intrinsic kinase activity. Specific binding of ¹²⁵I-labeled EGF, defined as counts of total ¹²⁵I EGF binding minus counts not displaced by a 100-fold excess of unlabeled EGF, did not change with addition of antibody (data not shown). This may be due to the location of the fusion junction at a site distant from the EGF binding domain at residues 351–364 (Wu, et al., J. Biol. Chem. (1989), 264:17469–17475). The kinase activity of the mutant EGFR did not change with the presence of antibody, as assessed by band intensity in autoradiography of an SDS-polyacrylamide gel (data not shown).

Internalization of Antipeptide IgG

Binding of antipeptide IgG to live tumor cells was determined by immunofluorescence assay. D-270 MG-X or A431-X cells were prepared by dissociation from tumor xenografts grown subcutaneously in athymic mice. Briefly, subcutaneous tumors were removed from the mouse and the viable portions were separated from areas of necrosis. The viable tissue was minced with scissors and dissociated into a single cell suspension by incubating 1 hr in 0.8% collagenase at 37° C. in a trypsinization flask. The cells were washed twice with cold Richter's zinc-option medium containing 1% normal goat serum. One million viable cells, as assessed by trypan blue, were incubated 30 min at 4° C. with zinc-option medium plus 10% normal goat serum to block nonspecific binding. The cells were incubated 30 min at 4° C. with 100 μl of antipeptide antibody (20 μg per ml) or pre-immune IgG. After washing 3 times with zinc-option medium plus 1% normal goat serum, the cells were incubated with 100 μl of fluorescein-labeled goat antirabbit IgG for 30 min at 4° C. The cells were washed as above and resuspended in 500 μl of cold zinc-option medium plus 1% normal goat serum. One-hundred-microliter aliquots were removed and warmed to 37° C. for 10 to 60 min and observed with a Zeiss fluorescent microscope.

The anti-synthetic peptide antibody rapidly bound the surface mutant EGFR expressed on live glioma D-270 MG-X cells, and this binding was reflected by a rimming pattern of the immunofluorescent secondary antibody label. Internationalization rapidly ensued and was manifested as a speckled intracytoplasmic morphology. Internalization with loss of the peripheral plasma membrane rimming was complete by 60 min at 37° C.

Immunoprecipitation of EGFR

EGFR from xenograft tissue was solubilized and immunoprecipitated as follows. Ten mg of frozen (−70° C.) xenograft tissue were homogenized in 1 ml of ice-cold solubilization buffer composed of 20 mM Iodoacetate, and Aprotinin at 1 mg/ml. After 2 h at 4° C., the preparation was centrifuged for 15 min at 4° C. in a Beckman tabletop centrifuge at 12,000×g. The supernatant was used in EGFR immunoprecipitation. Immunoprecipitation was performed with monoclonal antibody Ab-1 (clone 528: Oncogene Science, Inc.), reactive against the normal external domain of EGFR.

Monoclonal antibody Ab-1 (528) is an IgG2a which inhibits EGF binding to its receptor. For each reaction mixture, 5 ug of monoclonal antibody Ab-1 (528) or 15 ul of undiluted antiserum containing polyclonal antibody were bound to 2 mg of Protein A-Sepharose 4B by incubation in 115 mM sodium phosphate buffer, pH 7.4, for 30 min at room temperature. Antibody-Protein A-Sepharose complex was washed 3 times with 115 mM sodium phosphate buffer, pH 7.4 EGFR immunoprecipitation was performed with 500-ul aliquots of solubilized xenograft tissue, 500 ul of 115 mM sodium phosphate buffer, pH 7.4, and the antibody-Protein A-Sepharose pellet.

After pellet resuspension, overnight incubation was done at 4° C. Immunoprecipitates were washed 3 times with 1 ml of solubilization buffer, and the pellet was used for autophosphorylation.

Autophosphorylation of EGFR

Autophorylation of the immunoprecipitated EGFR was performed. The EGFR-antibody-Protein A-Sepharose pellets were incubated with 30 ul of solubilization buffer plus 2 mM MnCl₂ and 3 uCi of gamma-[³²P]ATP (New England Nuclear; 2000 to 3000 Ci/m-mol). After reaction for 10 min at 4° C. on ice, the reaction was terminated by the addition of 30 ul of 2× Laemmli SDS-PAGE sample buffer with 2% B-mercaptoethanol. Samples were boiled for 3 min and centrifuged. Supernatants were used in loading SDS-polyacrylamide gels.

Immunoblot Analysis

Western immunoblot analysis was performed with the use of a semidry horizontal electrophoretic transfer system with graphite electrodes (LKB Multiphor II Nova Blot System). Briefly, frozen A431 and glioma xenografts were solubilized in SDS-gel sample buffer, boiled, and electrophoresed in a 7.5% SDS-polyacrylamide gel. The proteins were transferred to nitrocellulosse at 150 mA for 2 h, and immunohistochemical detection of EGFR was accomplished with antibody 528 and polyclonal antisera from rabbit no. 4 directed against a type II peptide.

Polyclonal antibodies against the Type II mutants are tissue specific within the limits of present testing. See, FIGS. 9 and 10.

The patents and literature articles cited in this disclosure are expressly incorporated herein by reference.

We claim:

1. An EGFR peptide which is less than 50 amino acids in length, said peptide bearing a type II mutation of EGFR, said mutation being characterized by including the sequence LYS-LYS-GLY-ASN-TYR.

2. The EGFR peptide of claim 1, said peptide consisting of LEU-GLU-GLU-LYS-LYS-GLY-ASN-TYR-VAL-VAL-THR.

3. The EGFR peptide of claim 1 which is at least 10 amino acids in length.

4. The EGFR peptide of claim 1 which is 14 amino acids in length.

5. The EGFR peptide of claim 1 which is 11 amino acids in length.

6. The EGFR peptide of claim 1 which is coupled to a larger immunogenic substance.

7. The EGFR peptide of claim 6 wherein said large immunogenic substance is keyhole limpet hemocyanin.

8. The EGFR peptide of claim 1 which is coupled to an inert matrix.

9. The EGFR peptide of claim 8 wherein said indent matrix is agarose beads.

10. The EGFR peptide of claim 1 which is coupled to a larger inert protein.

11. The EGFR peptide of claim 10 wherein said larger inert protein is bovine serum albumin.

12. The EGFR peptide of claim 1 which consists of a linear sequence of amino acids, said sequence being: LEU-GLU-GLU-LYS-LYS-GLY-ASN-TYR-VAL-VAL-THR-ASP-HIS-CYS.

* * * * *

UNITED STATES PATENT AND TRADEMARK OFFICE
CERTIFICATE OF CORRECTION

PATENT NO. : 5,401,828
DATED : March 28, 1995
INVENTOR(S) : Bert Vogelstein and Darell Bigner It is certified that error appears in the above-indentified patent and that said Letters Patent is hereby corrected as shown below:

On the title page, item [56]

REFERENCES CITED

Please add the following references:

Bartels et al., *Am. J. Hum. Genet.* 38:280-287 (1986)

Bigner et al., *Cancer Genet. Cytogenetics* 22:121-135 (1986)

Bigner et al., *J. Neuropathol. Ex. Neurol.* 47:191-205 (1988)

Bullard et al., *J. Neurosurg.* 64:257-262 (1986)

Di Fiore et al., *Cell* 51:1063-1070 (1987)

Downward et al., *Nature* 307:521-527 (1984)

Fung et al., *Cell* 33:357-368 (1984)

Gammett et al., *Proc. Natl. Acad. Sci. USA* 83:6053-6057 (1986)

UNITED STATES PATENT AND TRADEMARK OFFICE
CERTIFICATE OF CORRECTION

PATENT NO. : 5,401,828
DATED : March 28, 1995
INVENTOR(S) : Bert Vogelstein and Darell Bigner It is certified that error appears in the above-indentified patent and that said Letters Patent is hereby corrected as shown below:

Haley et al., *Oncogenes and Growth Factors*, edited by Guroff, G. 12th Edition, Chapter 2, pp. 40-76, Wiley, New York (1987A)

Signed and Sealed this

Fourth Day of July, 1995

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,401,828
DATED : March 28, 1995
INVENTOR(S) : Bert Vogelstein et al.

It is certified that error appears in the above-identified patent and that said Letters Patent is hereby corrected as shown below:

<u>Title page,</u>
Item [75], Inventors, please insert -- Albert J. Wong, Philadelphia, PA (US) --

Signed and Sealed this

Thirteenth Day of July, 2004

JON W. DUDAS
*Acting Director of the United States Patent and Trademark Office*